US012364846B1

(12) United States Patent
Arthur et al.

(10) Patent No.: US 12,364,846 B1
(45) Date of Patent: Jul. 22, 2025

(54) SYSTEMS AND METHODS FOR ARTERIAL ACCESS, DIAGNOSIS, AND THERAPY

(71) Applicant: Direct External Carotid Access LLC, Germantown, TN (US)

(72) Inventors: Adam S. Arthur, Memphis, TN (US); David Fiorella, Stony Brook, NY (US); Kevin T. Foley, Germantown, TN (US)

(73) Assignee: Direct External Carotid Access LLC, Germantown, TN (US)

( * ) Notice: Subject to any disclaimer, the term of this patent is extended or adjusted under 35 U.S.C. 154(b) by 0 days.

(21) Appl. No.: 18/755,607

(22) Filed: Jun. 26, 2024

(51) Int. Cl.
*A61M 39/02* (2006.01)
(52) U.S. Cl.
CPC . *A61M 39/0208* (2013.01); *A61M 2039/0258* (2013.01); *A61M 2205/0266* (2013.01); *A61M 2210/005* (2013.01); *A61M 2210/06* (2013.01)
(58) Field of Classification Search
CPC ...... A61M 39/0208; A61M 2039/0258; A61M 2205/0266; A61M 2210/005; A61M 2210/06
See application file for complete search history.

(56) References Cited

U.S. PATENT DOCUMENTS

2007/0255234 A1\* 11/2007 Haase ............... A61M 5/14276
604/288.01
2013/0281788 A1\* 10/2013 Garrison ............. A61B 17/221
606/127

(Continued)

OTHER PUBLICATIONS

Gobin Y, Pasco A, Merland J, Aymard A, Casaco A, Houdart E, "Percutaneous puncture of the external carotid artery or its branches after surgical ligation," American Journal of Neuroradiology, 1994, vol. 15, No. 1, pp. 79-82. http://www.ajnr.org/content/15/1/79.

(Continued)

*Primary Examiner* — Alireza Nia
*Assistant Examiner* — Hamza A Darb
(74) *Attorney, Agent, or Firm* — BLAIR WALKER IP SERVICES, LLC

(57) ABSTRACT

A system for accessing one or more artery in a head and neck area of a patient includes an access sheath including a tubular shaft having a distal end and a proximal end and a sheath lumen extending therethrough, the distal end of the shaft configured for placement through a puncture in skin and an adjacent arterial wall of a superficial temporal artery of a subject and to extend retrogradely within a portion of the superficial temporal artery of the subject, the proximal end of the shaft including a first connection portion, an intermediate portion of the sheath located between the distal end of the shaft and the proximal end of the shaft, the intermediate portion forming a curve of the sheath lumen, a resilient access-extension tube having an extension lumen extending therethrough, the extension lumen having a distal end and a proximal end, the distal end of the extension lumen configured to hydraulically couple to the sheath lumen at the first connection portion, and sealable opening carried by the access-extension tube and spaced from the distal end of the extension lumen, the sealable opening configured to allow insertion of an elongate medical device into the extension lumen for advancement through the extension lumen when the access-extension tube is coupled to the access sheath, for passage through the extension tube and the sheath lumen, and into the superficial temporal artery of the subject.

30 Claims, 25 Drawing Sheets

(56) References Cited

U.S. PATENT DOCUMENTS

| | | | |
|---|---|---|---|
| 2014/0018788 A1 | 1/2014 | Engelman et al. | |
| 2014/0243809 A1* | 8/2014 | Gelfand | A61B 18/1492 606/41 |
| 2016/0015938 A1* | 1/2016 | Ehrlich | A61B 5/6803 604/179 |

OTHER PUBLICATIONS

Oh J-S, Yoon S-M, Shim J-J, Bae H-G, "Transcranciial Direct Middle Meningeal Artery Puncture for the Onyx Embolization of Dural Arteriovenous Fistula Involving the Superior Sagittal Sinus," Journal of the Korean Neurosurgical Society, 2015, vol. 57, No. 1, pp. 54-57.

Graham E, Orjuela K, Poisson S, Biller J, "Treatment challenges in idiopathic extracranial ICA vasospasm case report and review of the literature," eNeurosurgicalSci, 2021, vol. 22, pp. 1-5. https://doi.org/10.1016/j.ensci.2020.100304.

Walker G, Wand A, Hadwen J, Erdenebold U-E, Bebedjian R, Sullivan P, Santos M, Chenier C, Karwaski S, CaronK, Varga G, Lyon J, Lesiuk H, Heran N, Heran M, Quateen A, Drake B, Portela De Oliveira E, Kontolemos M, Fahed R, "Direct Puncture of the Superficial Temporal Artery in Embolization of a Scalp Arteriovenous Fistula: A Case Report," Neurointervention, 2023, vol. 18, pp. 67-71. https://doi.org/10.5469/neuroint.2022.00465.

* cited by examiner

SYSTEMS AND METHODS FOR ARTERIAL ACCESS, DIAGNOSIS, AND THERAPY

FIELD OF THE INVENTION

The field of the invention generally relates to sheath and catheter systems for introducing elongate medical devices into the body and the treatment methods used therewith.

SUMMARY OF THE INVENTION

In one embodiment of the present disclosure, a system for accessing one or more artery in a head and neck area of a patient includes an access sheath including a tubular shaft having a distal end and a proximal end and a sheath lumen extending therethrough, the distal end of the shaft configured for placement through a puncture in skin and an adjacent arterial wall of a superficial temporal artery of a subject and to extend retrogradely within a portion of the superficial temporal artery of the subject, the proximal end of the shaft including a first connection portion, an intermediate portion of the sheath located between the distal end of the shaft and the proximal end of the shaft, the intermediate portion forming a substantially U-shape or J-shape of the sheath lumen, a resilient access-extension tube having an extension lumen extending therethrough, the extension lumen having a distal end and a proximal end, the distal end of the extension lumen configured to hydraulically couple to the sheath lumen at the first connection portion, and sealable opening carried by the access-extension tube and spaced from the distal end of the extension lumen, the sealable opening configured to allow insertion of an elongate medical device into the extension lumen for advancement through the extension lumen when the access-extension tube is coupled to the access sheath, for passage through the extension tube and the sheath lumen, and into the superficial temporal artery of the subject.

In another embodiment of the present disclosure a method for accessing one or more artery in a head and neck area of a patient includes creating an opening in skin an in an adjacent arterial wall of a superficial temporal artery of a subject, inserting through the opening a distal end of a tubular shaft of an access sheath, the shaft further including a proximal end including a first connection portion, and a sheath lumen extending therethrough, the sheath including an intermediate portion located between the distal end of the shaft and the proximal end of the shaft, the intermediate portion forming a curved shape of the sheath lumen, adjusting the shaft such that the distal end extends retrogradely within a portion of the superficial temporal artery of the subject, hydraulically coupling a distal end of an extension lumen of a resilient access-extension tube to the first connection portion, the extension lumen further including a proximal end, the extension lumen extending through the access-extension tube, the access extension tube further carrying a sealable opening, inserting an elongate medical device through the sealable opening and into the extension lumen and advancing the device through the extension lumen and the sheath lumen, and advancing the medical device retrogradely through at least a portion of the superficial temporal artery of the subject, and performing a medical procedure with the elongate medical device within the arterial system of the subject.

DETAILED DESCRIPTION

The disclosure generally relates to providing access to the branches of the external carotid artery or internal carotid artery to allow the delivery of drugs, embolic materials, and devices to this region. The systems and methods presented herein reduce or remove the need to cannulate a peripheral artery in the arm or leg. They also obviate the need for the access system to traverse the aortic arch of the aorta, common carotid arteries, or any arteries that irrigate the brain, dramatically lowering the risk of thromboembolic stroke during such access. This is especially important in elderly patients. These techniques and systems for performing them avoid the traditional femoral artery access or radial artery access which are known to have increased risks for thromboembolic events. The procedures taught herein also limit the amount of contrast media needed (e.g., for angiography or fluoroscopy), because the aortic arch and the common carotid arteries would not need to be assessed for anatomy or size purposes, as they are not involved in the tracking of the devices. Because catheters do not need to be tracked through the aortic arch or the common carotid arteries, catheter-based risks of these areas do not exist. The procedures taught herein can also be more rapid to perform than the traditional procedures utilizing femoral or radial artery access (or other access points that require passage of the aortic arch and the common carotid arteries). The traditional procedures, especially in older patients, can be fraught with complications and difficulty passing diseased, or otherwise compromised vessels, significantly delaying the procedure.

Figure 1:
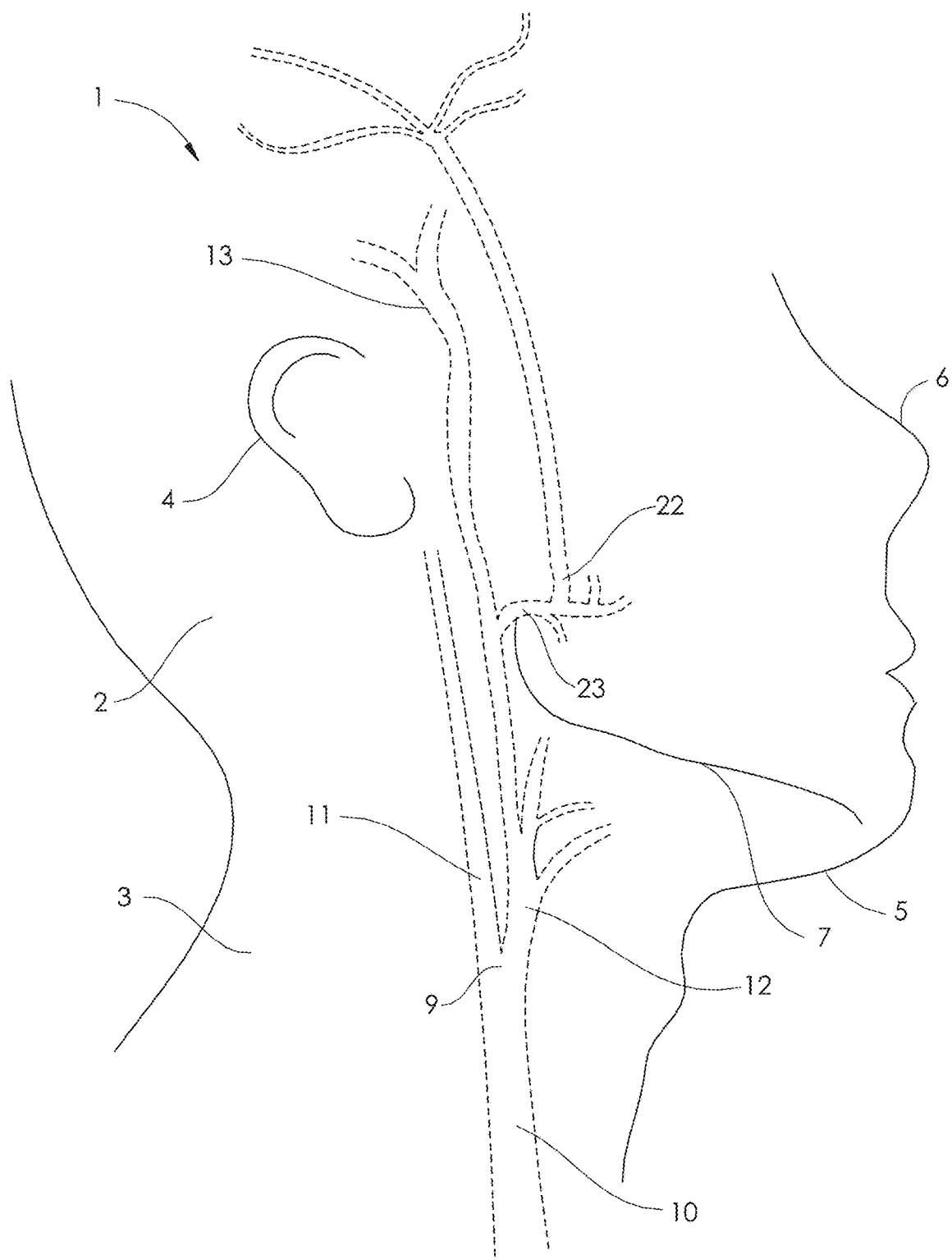
FIG. 1 is a right side view of the head of a patient, illustrating certain arteries of the head and neck.

FIG. 1 illustrates the head 2 of a patient 1, showing the patient's neck 3, right ear 4, chin 5, nose 6, and jawline 7. The right common carotid artery 10 delivers oxygenated blood from the aortic arch and brachiocephalic artery (in most patients) and brings it toward the head 2 to the right carotid bifurcation 9. At the bifurcation 9, the right internal carotid artery 11 delivers blood through the base of the skull and to the brain and the cerebral arterial circulation; the right external carotid artery 12 splits into the right superficial temporal artery 13 and the right internal maxillary artery (rIMAX) 23. The right middle meningeal artery (rMMA) 22 commonly branches off from the right internal maxillary artery (rIMAX) 23. The similar arteries on the left side of the head follow similar paths, except that, most commonly, the left common carotid artery and the left subclavian artery each branch directly from the aortic arch. Thus, there is most commonly no left brachiocephalic artery in patients. Throughout this disclosure, the embodiments will describe use in the right arterial system of the head and neck. However, in each embodiment, the left arterial system can also be accessed in much of the same manner.

Figure 2:
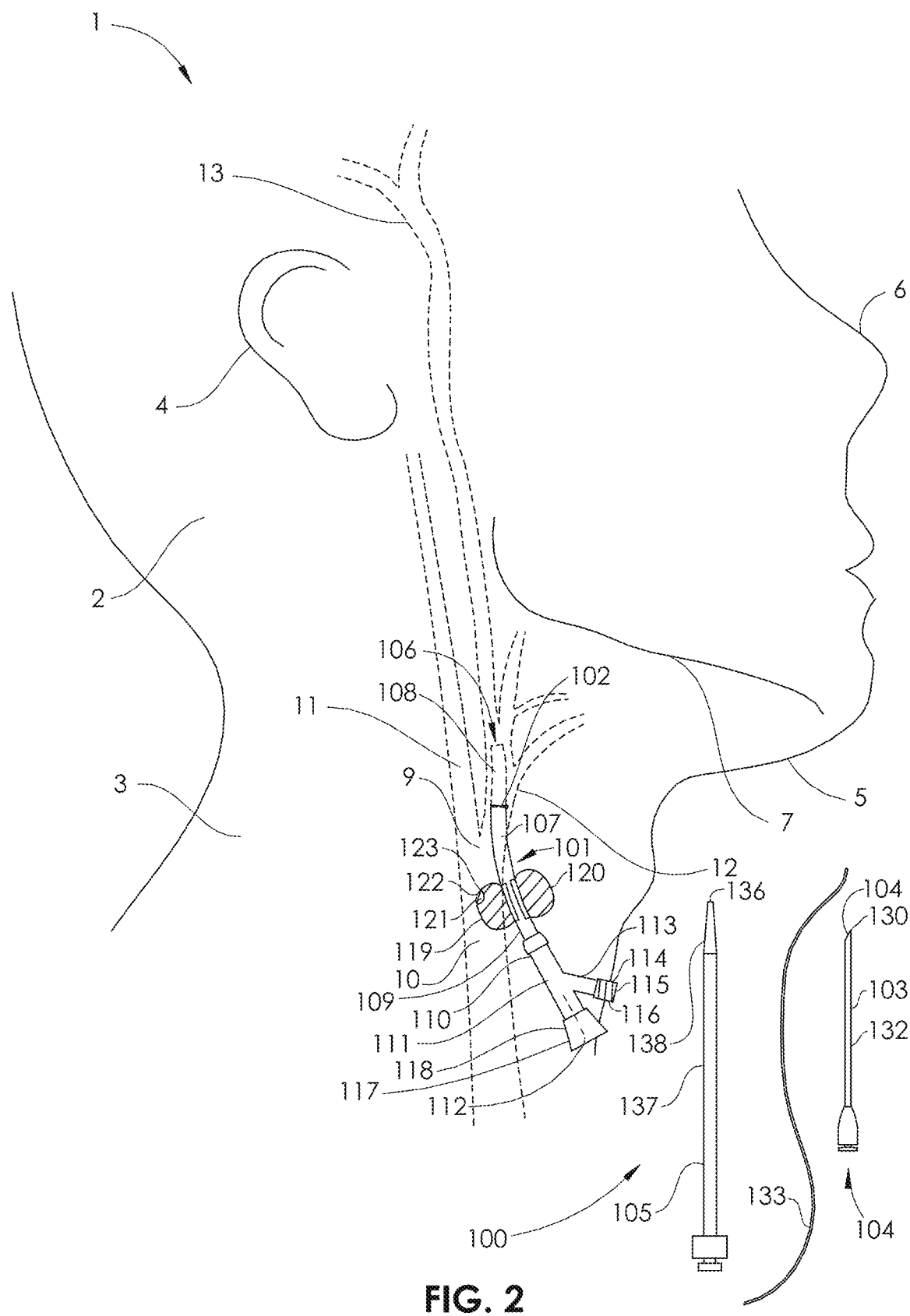
FIG. 2 is a right side view of the head of a patient illustrating a sheath placed directly into the right external carotid of a patient via direct puncture, according to an embodiment of the present disclosure.

FIG. 2 illustrates an access and treatment system 100, according to a first embodiment, comprising an external carotid access sheath 101 configured to be inserted antegradely through a dilated puncture 102, utilizing the Seldinger technique. This technique involves puncture with a hypodermic needle 103, placement of a guidewire 133 antegradely through the lumen 104 of the needle and into the right external carotid artery 12, removal of the needle 103, and placement of the sheath 101 with a dilator 105 inserted therethrough antegradely into the right external carotid artery 12. And finally, removal of the dilator 105 from the lumen 106 of the sheath 101.

The sheath 101 comprises an elongate shaft 107 having a lumen 106 extending therethrough. The shaft 107 comprises a distal end 108 for insertion into a blood vessel, such as an artery, for example an external carotid artery 12. In some embodiments, the distal end 108 can be advanced into branches of the external carotid artery 12 and in some embodiments into branches of these branches. The shaft 107 further comprises a proximal end 109 that is coupled to a distal end 110 of a connector 111. The connector 111 includes a through lumen 112 that is hydraulically coupled to the lumen 106 and configured such that the dilator 105 or other elongate devices can be placed through both the lumen 112 and the lumen 106. The connector 111 further comprises a side port 113 having a female luer connector 114 having a female luer taper 115 and a male luer lock thread 116. In other embodiments, the side port 113 can be coupled to an extension tube having a male luer connector at one end and another connector (e.g., a female luer connector) at the other end. In other embodiments, the side port 113 can be replaced by an extension tube having one end that is hydraulically coupled to the lumen 112 and another end having a female luer connector. A proximal end 118 of the connector 111 includes a valve 117 configured for sealingly placing elongate devices through. In some embodiments, the valve 117 comprises a duckbill valve. In some embodiments, the valve 117 comprises a Touhy-Borst valve. In some embodiments, the valve 117 comprises an axially-spring-loaded open/close valve.

Once the shaft 107 of the sheath 101 is inserted to a desired depth of insertion into the arterial system via the dilated puncture 102 into the right external carotid artery 12, the sheath 101 is further configured to be secured to the skin of the neck 3 of the patient 1. Two wings 119, 120 each extend laterally from the longitudinal axis of the shaft 107, opposite of each other. The wings 119, 120 are in some embodiments insert molded onto the shaft 107. In other embodiments, the wings 119, 120 each include an elongate semi-cylindrical cavity which is secured to an outer portion of the shaft 107 with an adhesive, epoxy, hot melt, or thermally bonded. The wings 119, 120 each have at least one planar, substantially flat, or curved side 123 which include an adhesive 121. The adhesive 121 can be exposed by a user by removing a peel-away strip 122. In some embodiments, the sides 123 comprise an overall curve having a radius of curvature that is configured to substantially match typical curvatures of patient necks 3. In some embodiments, the radius of curvature can comprise 5 mm to 12 mm, or 6 mm to 9 mm. After cleaning the neck 3 of the patient 1, the peel-away strips 122 are removed from the wings 119, 120 and the adhesive 121 (e.g., adhesive strips) are pressed against the neck 3 to secure the wings 119, 120, thus maintaining the longitudinal position of the shaft 107 of the sheath 101.

Figure 3:
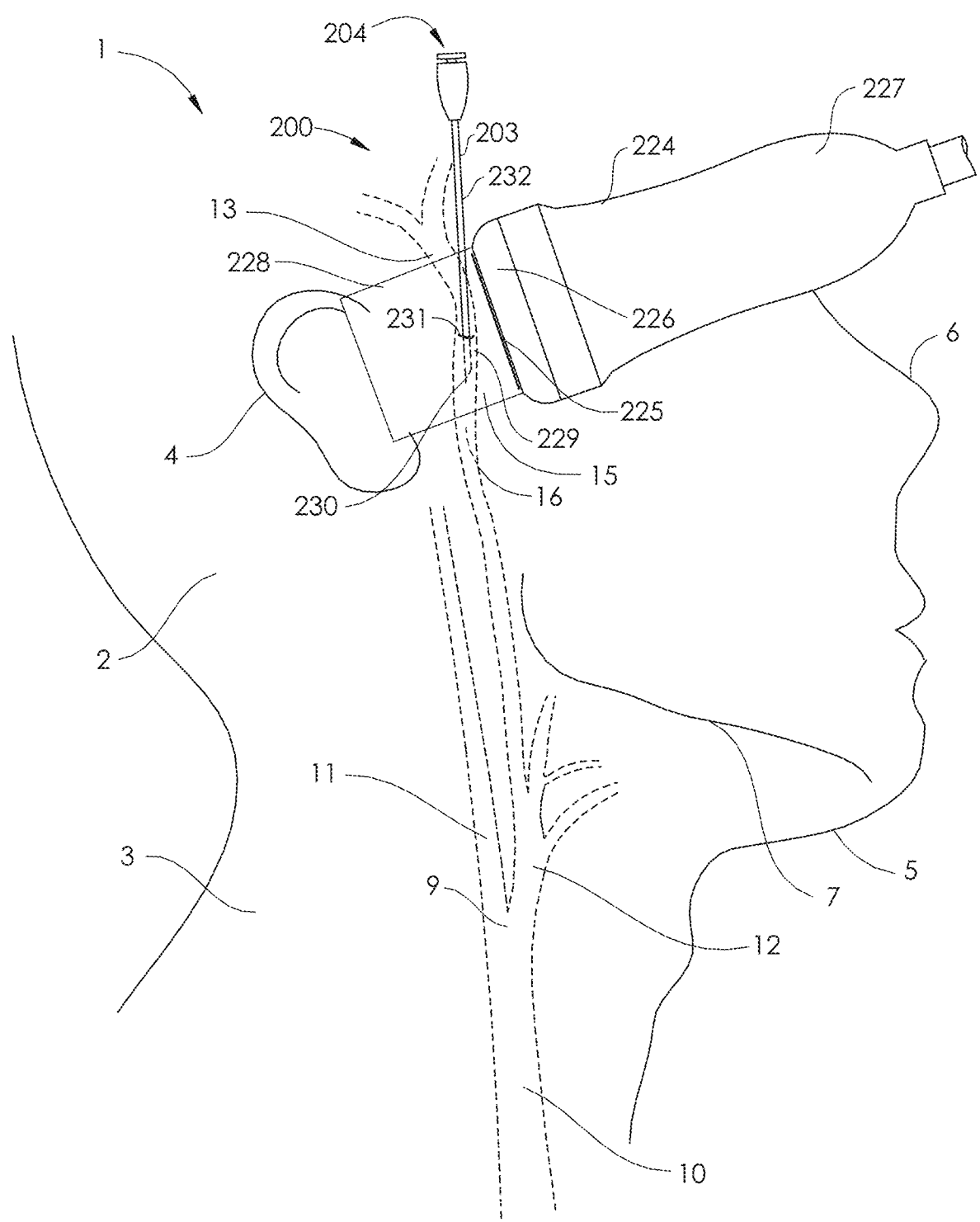
FIG. 3 is a right side view of the head of a patient illustrating the placement of a hypodermic needle into the right superficial temporal artery of a patient via direct puncture with the aid of ultrasound visualization, according to an embodiment of the present disclosure.

FIGS. 3-7 illustrate the placement and delivery of an access and treatment system 200, according to a second embodiment. First, a skin portion 15 of the patient 1, located in the vicinity of the sideburn, superior to the location of the zygoma, is shaved down as necessary. In some cases, the patient 1 is treated while awake, using local anesthesia near the skin portion 15. In other cases, it may be desirable to have the patient 1 under general anesthesia, depending on what particular malady is being treated, and what the condition of the patient is. For good access in a supine patient 1, the head 2 is positioned turned to the left for access to one or more right side arteries, and positioned turned to the right for access to one or more left side arteries. In FIG. 3, An ultrasound probe 224 is placed by a user on the skin portion 15 of the patient 1, with some gel 225 between the head 226 of the ultrasound probe 224 and the skin portion 15. The ultrasound probe 224 is configured to operate at a frequency of between about 5 MHz and about 15 MHz, or between about 10 MHz and about 15 MHz, in order to provide sufficient depth of penetration and resolution in a sizable percentage of patients. In some embodiments, the ultrasound is configured to utilize Doppler to identify the location of the right superficial temporal artery 13 by flow. In FIG. 3, the ultrasound probe 224 is a linear array device, and is shown with the proximal end 227 rotated significantly anteriorly. This particular position allows an especially clear depiction and view of all elements of the drawing. However, the ultrasound probe 224 can be utilized in any one of a number of different orientations to provide a favorable image of the right superficial temporal artery 13, or, if using Doppler, of favorably identifying the right superficial temporal artery 13 by flow. For example, the proximal end 227 of the ultrasound probe 224 can be extended substantially laterally to the head 12 (i.e., sticking straight up out of the drawing), or can have some or a large amount of angulation anteriorly, posteriorly, superiorly, inferiorly, or a combination of one or more of these, depending on the anatomy of the patient: including skin or cranial contours, the presence of scars or injured or diseased areas, or the location and angulation of the desired access artery (e.g., superficial temporal artery 13).

Figure 4:
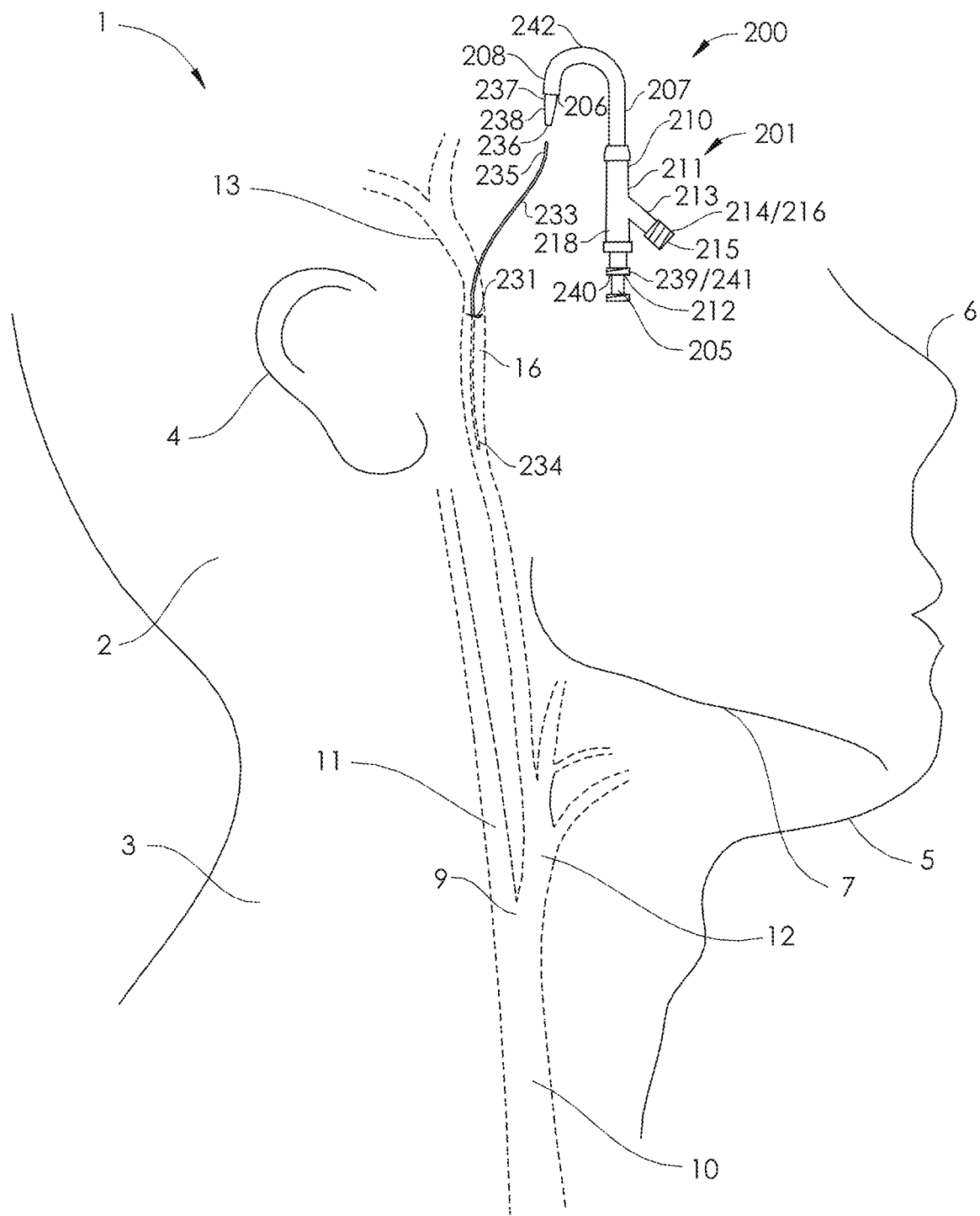
FIG. 4 is a right side view of the head of the patient illustrating a guidewire that was placed through a needle and is being backloaded through a curveable dilator and a curved sheath, according to an embodiment of the present disclosure.
Figure 5:
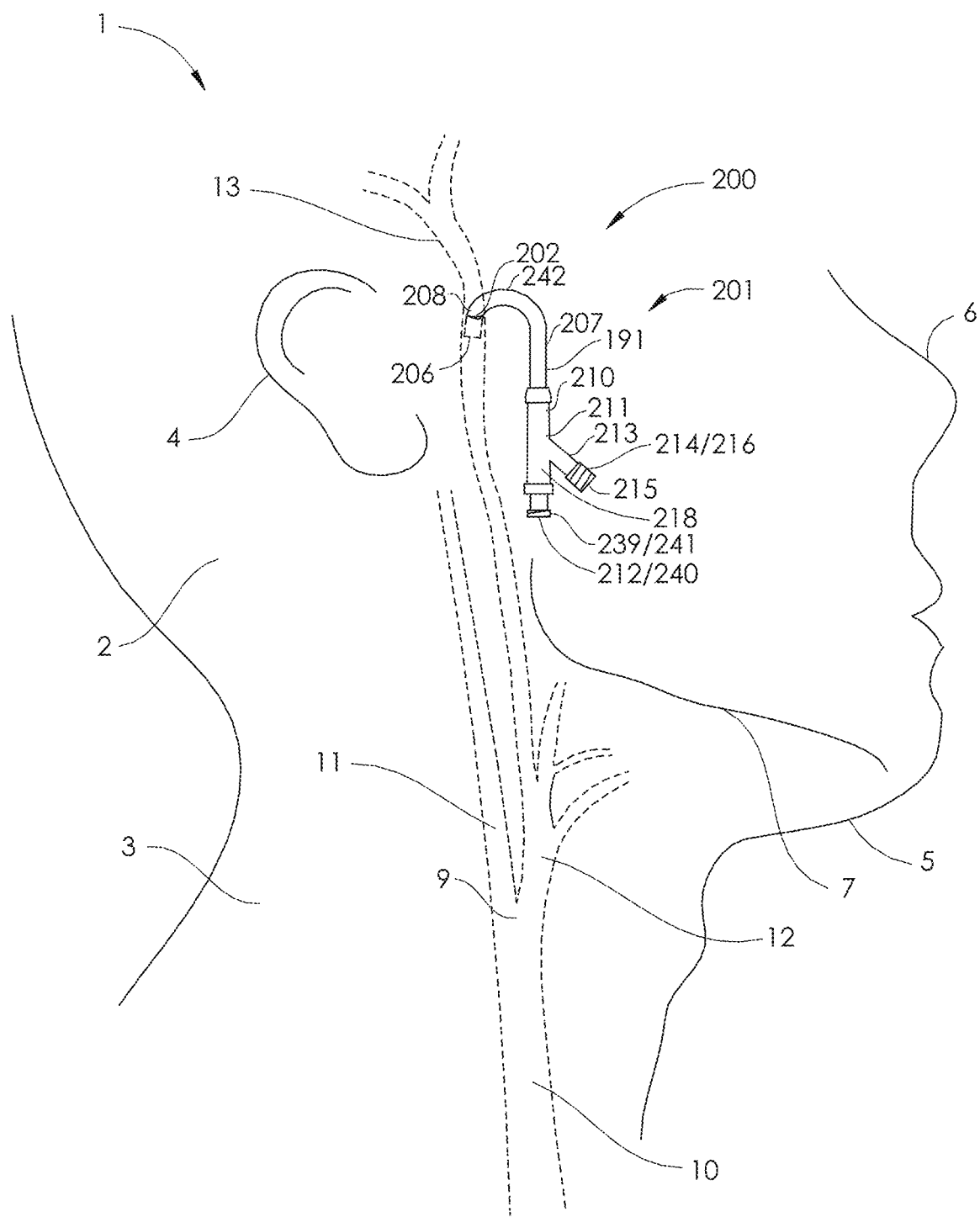
FIG. 5 is a right side view of the head of the patient illustrating the curved sheath placed through a puncture, with the dilator removed, according to an embodiment of the present disclosure.

The linear array of the ultrasound probe 224 produces a linear field of view 228 that includes the general target entry area 229 of the right superficial temporal artery 13, when placed properly. Or, that targets the superficial temporal artery 13 at the general target entry area 229 for Doppler identification of flow. In other embodiments, a phased array ultrasound probe 224 can be utilized, to provide a sector field of view, or curved linear array ultrasound probe 224 can be utilized to provide a sector field of view. The distal tip 230 of a hypodermic needle 203 is placed through the skin at the skin portion 15 under ultrasound guidance to create a needle puncture 231, and a portion of the needle shaft 232 is advanced into the lumen 16 of the right superficial temporal artery 13. A guidewire 233 is inserted into the lumen 204 of the needle 203, and advanced into the lumen 16 of the right superficial temporal artery 13. The needle 203 is then removed, as shown in FIG. 4, and the distal end 234 of the guidewire 233 extends into the lumen 16 of the right superficial temporal artery 13, while the proximal end 235 of the guidewire 233 extends from the needle puncture 231. The proximal end 235 of the guidewire 233 is now inserted (backloaded) into the dilator lumen 236 that extends through the shaft 237 of the dilator 205. Then, the tapered distal tip 238 of the dilator 205 and the distal end 208 of a curved sheath are advanced through the needle puncture 231, dilating it such that it is stretched or otherwise increased to be a dilated puncture 202 (FIG. 5). The ultrasound guidance is helpful to identify the location of the straight segments and tortuous segments of the superficial temporal artery 13 or the internal maxillary artery 23.

Figure 6:
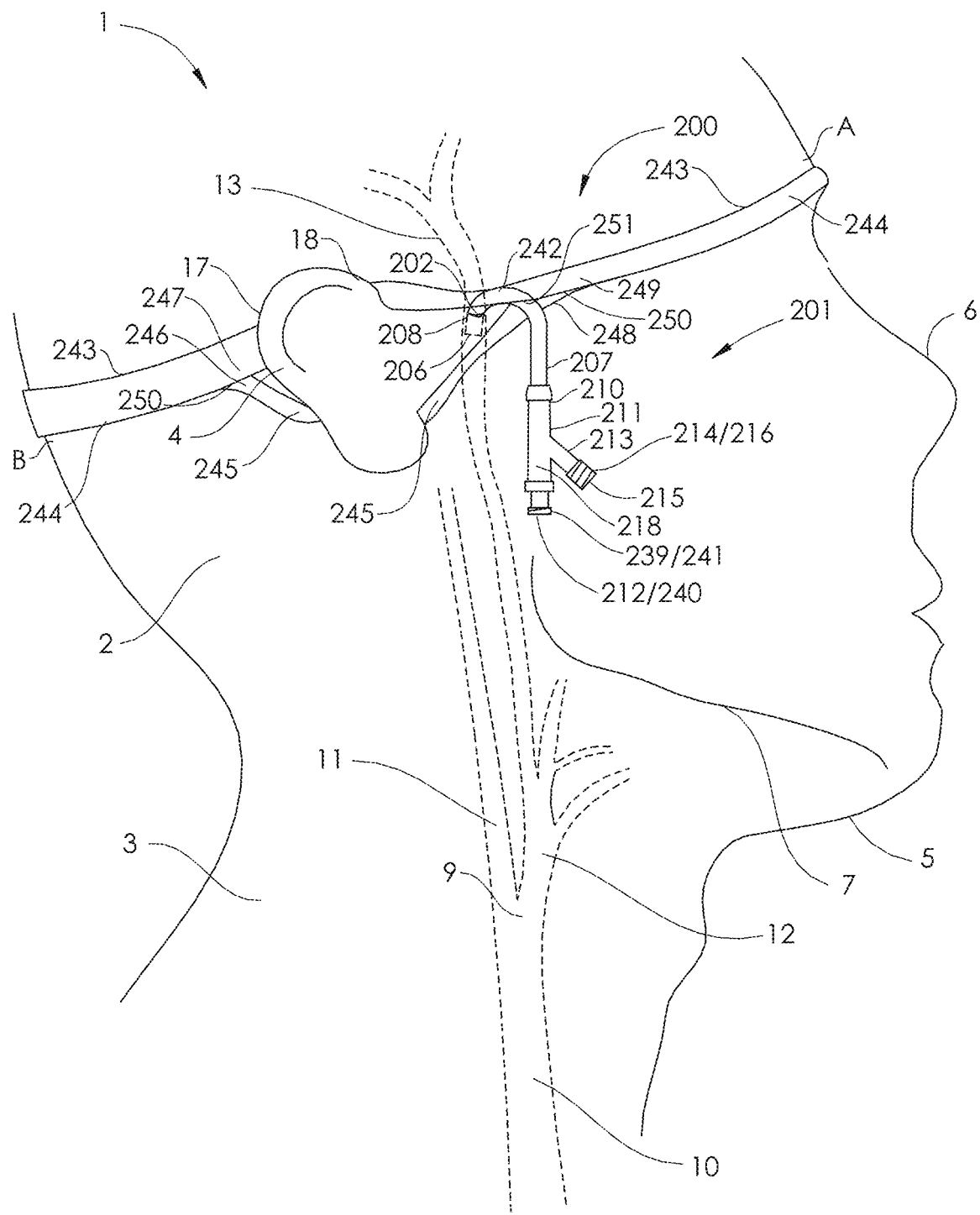
FIG. 6 is a right side view of the head of the patient illustrating the curved sheath canalizing the right superficial temporal artery of the patient and held in position with a strap or band, according to an embodiment of the present disclosure.
Figure 7:
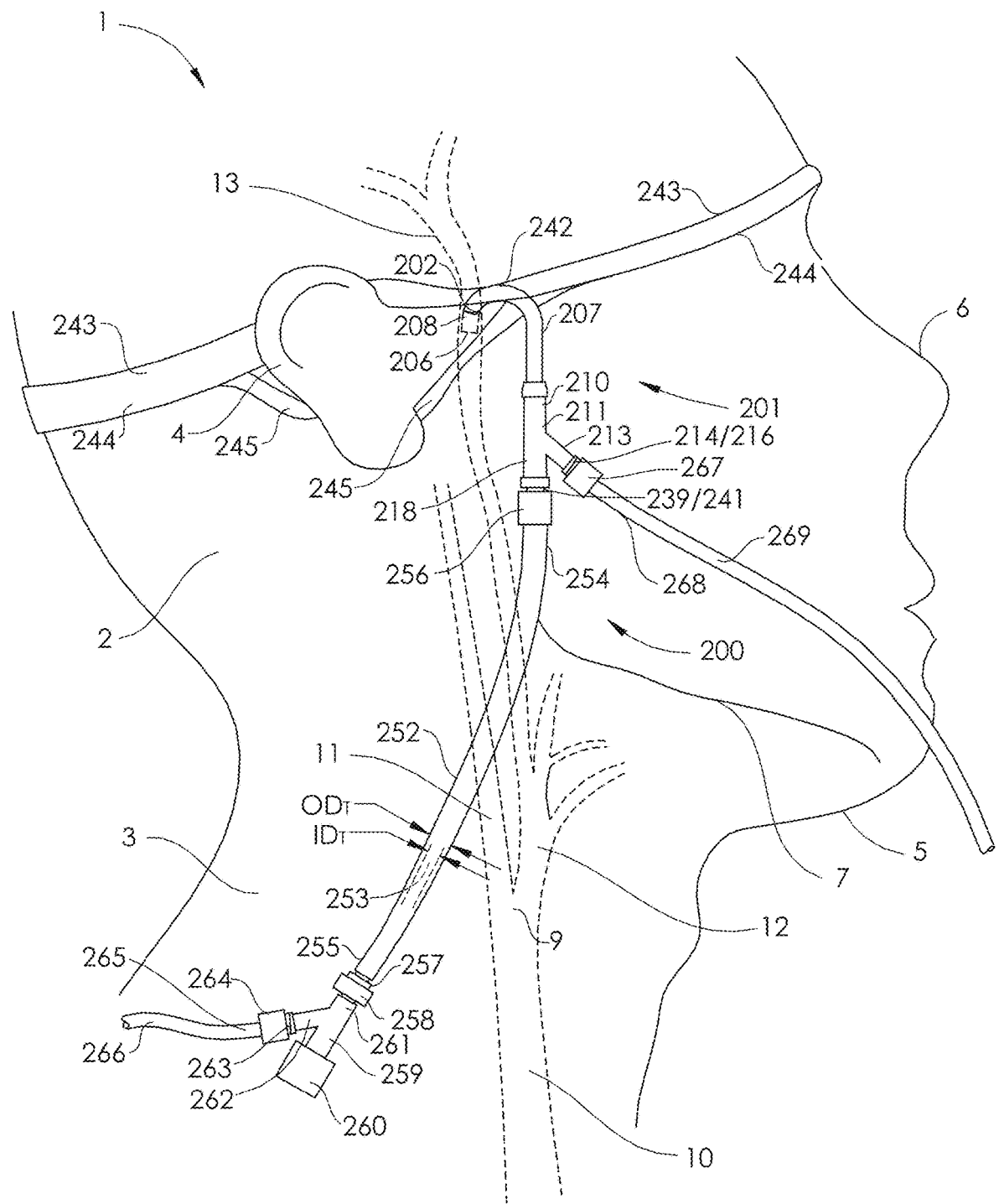
FIG. 7 is a right side view of the head of the patient illustrating a flexible tube and rotating hemostatic valve connected to the curved sheath, according to an embodiment of the present disclosure.

The curved sheath 201 comprises an elongate shaft 207 having a lumen 206 extending therethrough. The shaft 207 comprises a distal end 208 for insertion into a blood vessel, such as an artery, for example the right superficial temporal artery 13, and a U-shaped curve 242. The U-shaped curve 242 is configured to orient both the distal end 208 of the shaft 207 of the curved sheath 201 and the proximal end 218 of a connector 211 of the curved sheath 201 such that they substantially extend in the same direction as each other. In the clinical configurations or clinical cases illustrated in FIGS. 3-15 and 17, the direction the distal end 208 of the shaft 207 of the curved sheath 201 and the proximal end 218 of a connector 211 of the curved sheath 201 both point is generally inferiorly. In some embodiments, the distal end 208 of the shaft 207 can be advanced into branches of the arterial system that include many branches between the dilated puncture 202 and the right bifurcation 9, and even to the right common carotid artery 10 and the right internal carotid artery 11. The shaft 207 further comprises a proximal end 209 that is coupled to a distal end 210 of the connector 211. The connector 211 includes a through lumen 212 that is hydraulically coupled to the lumen 206 and configured such that the dilator 205 or other elongate devices can be placed through both the lumen 212 and the lumen 206. The connector 211 further comprises a side port 213 having a female luer connector 214 having a female luer taper 215 and a male luer lock thread 216. In other embodiments, the side port 213 can be coupled to an extension tube having a male luer connector at one end and another connector (e.g., a female luer connector) at the other end. In other embodiments, the side port 213 can be replaced by an extension tube having one end that is hydraulically coupled to the lumen 212 and another end having a female luer connector. The female luer connector 214 is configured to be hydraulically coupled to a male luer connector 267 at a distal end 268 of an infusion or aspiration line 269, as shown in FIG. 7.

A proximal end 218 of the connector 211 comprises a female luer connector 239 having a female luer taper 240 and a male luer lock thread 241. In other embodiments, the proximal end 218 of the connector 211 includes a valve configured for sealingly placing elongate devices through. In some embodiments, the valve comprises a duckbill valve. In some embodiments, the valve comprises a Touhy-Borst valve. In some embodiments, the valve comprises an axially-spring-loaded open/close valve.

Turning to FIG. 5, the dilator 205 and the guidewire 233 are now retracted from the curved sheath 201, and are removed. The through lumen 212 now gives access via the female luer connector 239 to the entirety of the lumen 206 of the curved sheath 201. The U-shaped curve 242 comprises a substantially 180° curve. This allows both the retrograde entry and retrograde access to the right superficial temporal artery 13, and the procedural location for the hands of the user over the lower neck 3 and/or torso and/or groin area of the patient 1, as will be further detailed. In some embodiments, the U-shaped curve 242 can be replaced by any curve having a curvature (turn, e.g., hairpin turn) of between about 90° and about 270°, or between about 120° and about 240°, or between about 150° and about 210°, or between about 160° and about 200°, or between about 170° and about 190°, or between about 175° and about 185°. Thus, the U-shaped curve 242 can alternatively comprise a C-shaped curve, a J-shaped curve, or even a substantially L-shaped curve. Though the shaft 207 is shown in FIG. 5 as an overall J-shape, the U-shaped curve 242 portion is a U-shape. A straight portion 191 of the shaft 207 completes the overall J-shape. The U-shaped curve 242 is in some embodiments formed by placing a straight portion of the shaft 207 into a curved glass tube, with a flexible mandrel inserted snugly within the lumen 206, the glass tube having an inner diameter slightly larger than an outer diameter of the shaft 207, and then heating the glass tube and the shaft 207 material, and cooling them, to permanently set the U-shaped curve 242, even after the shaft 207 is removed from the glass tube and the mandrel is removed from the lumen 206. In other embodiments, the U-shaped curve 242 can be heat set in a similar manner, but using a clamshell mold, instead of the glass tube. Each half of the clamshell mold includes a matching curved cavity comprising a concave semi-circular indentation. In other embodiments, the U-shaped curve 242 can be curvably formed during the process of cooling (e.g., water cooling) immediately following extrusion of the shaft 207. Though the U-shaped curve 242 can have some flexibility or bendability, it tends to stay generally in the U-shape, having some built-in material memory to do so. The U-shaped curve 242 provides a U-shaped lumen 206 at the U-shaped curve 242. Alternatively, the U-shaped curve 242 and U-shaped lumen 206 can be caused by an external clip that holds the shaft 207 in this U-shape.

The shaft 207 can comprise a lubricious inner tubular layer ("liner") comprising a fluoropolymer such as PTFE (polytetrafluoroethylene), FEP (fluorinated ethylene propylene), PFA (perfluoroalkoxy alkane), ETFE (ethylene tetrafluoroethylene), or ECTFE (ethylene chlorotriflouroethylene). The shaft 207 can further comprise a tubular braid layer for reinforcement and torqueability, if needed, and/or a helical coil reinforcement layer, and/or a laser-machined hypo tube skeleton. The materials of these structures can comprise metallic materials such as stainless steel. An outer portion of the shaft 207 can comprise a tubular body structure comprising a polymer, such as polyurethane, polyamide, or polyether block amide. The distal end 208 of the shaft 207 can comprise a soft tip, for example comprising a lower flexural modulus than the rest of the shaft 207, and can also be absent of any metallic reinforcement layer. The softer tip protects the inner wall of the artery during canalization and positioning. The amount that the distal end 208 inserts into the artery can be relatively short, for example, one-half cm to four cm, or two cm to four cm.

The U-shaped curve 242 is configured to substantially stay in place when canalized into an artery (e.g., through the dilated puncture 202 into the right superficial temporal artery 13). However, in a procedure, where many manipulations occur, and other patient-health-related operations are occurring, it can be desirable to further increase the stability of the canalization of the distal end 208 of the shaft 207 of the curved sheath 201 into the right superficial temporal artery 13. Turning to FIG. 6, a securement band 243 is configured to stabilize the U-shaped curve 242 generally to the head 2 of the patient 1, and guard against disruption of its position and the overall position of the curved sheath 201. For example, if make it difficult for the distal end 208 of the shaft 207 to pull out of the dilated puncture 202. The securement band 243 comprises a continuous elastic head band 244 that is generally biased to a circumference that is less than a circumference of the head 2 of the patient 1 that extends around the head 2 of the patient 1 and traverses a point A and a point B. Point A is slightly above an eyebrow of the patient 1 and point B is at the back of the head 2 toward the top of the occipital bone. The circumference of the elastic head band 244 is configured to be stretched, causing an increasing bias caused by elastic material within the elastic head band 244, and reaching an increased diameter that is greater than the circumference of the head 2 of the patient 1 that extends around the head 2 of the patient 1 and traverses point A and point B. In alternative embodiments, the elastic head band 244, instead of being continuous, comprises an elastic or non-elastic linear, non-continuous band that can be tied to a desired circumference and/or amount of tightness around the head 2 of the patient 1 that extends around the head 2 of the patient 1 and traverses point A and point B.

The elastic head band 244 (or other band) acts a base structure. To this base structure, an ear loop 245 is secured. The ear loop 245 can comprise an elastic or non-elastic band, or a string or rope. The ear loop 245 in some embodiments comprises polymeric tape. A first end 246 of the ear loop 245 secures to a rear portion 247 of the elastic head band 244 that is configured to be located at or adjacent the posterior 17 of the ear 4 of the patient 1. A second end 248 of the ear loop 245 secures to a forward portion 249 of the elastic head band 244 that is configured to be located at or adjacent the anterior 18 of the ear 4 of the patient 1. The elastic head band 244 and the ear loop 245 can be thermally bonded to each other, or connected via sewing, stapling, adhesive, epoxy, or hot melt 250. The U-shaped curve 242 is secured to the elastic head band 244 and/or to the ear loop 245, for example with an adhesive, epoxy, or hot melt 251. Thus, the elastic head band 244 is configured to hook over the ear 4, and pass behind the superior crus of the ear and at least partially below the superior portion of the helix, while the ear loop 245 is configured to pass substantially below the ear 4. In the configuration shown in FIG. 6, the ear loop 245 also hooks underneath the ear lobe, though this is not a requirement, as ear lobes tend to have a variety of morphologies. The ear loop 245 in cooperation with the elastic head band 244 provide stability of the securement band 243 on the head 2 of the patient 1. The securement band 243 is maintained circumferential by one or both ears 4. Furthermore, the ear loop 245 maintains the vertical position of the distal end 208 of the shaft 207 of the curved sheath 201, keeping it from being pulled out from the dilated puncture 202. This increased stability allows a user (e.g., physician performing a procedure) to manipulate the connector 211 while able to rely on the access of the distal end 208 in the right superficial temporal artery 13, e.g., while attaching other elements or placing elongate devices into the lumen 206 and right superficial temporal artery 13 and removing elongate devices from the lumen 206 and right superficial temporal artery 13. In addition to the securement band 243, or as an alternative, the connector 211 can include suture tabs with suture holes, and can be sutured to the skin of the patient 1 for further stability. In other embodiments, the tabs can comprise adhesive tabs that can be adhered to the skin of the patient 1.

The user can insert elongate medical devices through the lumen 206 of the shaft 207 of the curved sheath 201 by directly inserting them into the lumen 212 of the connector 211 via the female luer connector 239. However, as shown in FIG. 7, the user can increase the ease of use in placing elongate medical products through the lumen 206 of the shaft 207 of the curved sheath 201 by the attachment of a second element of the access and treatment system 200: a flexible access tube 252. The flexible access tube 252 has an outer diameter $OD_T$ and an inner lumen 253 inner diameter $ID_T$. The inner diameter $ID_T$ is large enough to allow insertion and ease of longitudinal motion of catheters, guidewires, and probes having an outer diameter of up to 4.2 French (1.4 mm), and in some embodiments, larger than this. In some embodiments, the inner diameter $ID_T$ is between about 1.00 mm and about 1.96 mm, or between about 1.2 mm and about 1.6 mm. Thus, when the access tube 252 is coupled to the curved sheath 201, a 1.4 mm diameter distally-located maximum diameter portion of an elongate device can be passed through the inner lumen 253 of the access tube 252 and the lumen 206 of the curved sheath 201.

The flexible access tube 252 of the access and treatment system 200 can comprise a lubricious inner tubular layer ("liner") comprising a fluoropolymer such as PTFE (polytetrafluoroethylene), FEP (fluorinated ethylene propylene), PFA (perfluoroalkoxy alkane), ETFE (ethylene tetrafluoroethylene), or ECTFE (ethylene chlorotriflouroethylene). The flexible access tube 252 can further comprise a tubular braid layer for reinforcement and torqueability, if needed, and/or a helical coil reinforcement layer, and/or a laser-machined hypo tube skeleton. The materials of these structures can comprise metallic materials such as stainless steel. An outer portion of the flexible access tube 252 can comprise a tubular body structure comprising a polymer, such as polyurethane, polyamide, or polyether block amide. The reinforcement layer may not be required because torque requirements can be minimized or even eliminated by use of a rotating hemostatic valve (RHV) 259. The flexible access tube 252 comprises a distal end 254 and a proximal end 255. The distal end 254 is hydraulically coupled to a male luer connector 256, and the proximal end 255 is hydraulically coupled to a female luer connector 257. The male luer connector 256 is configured to be hydraulically coupled to the female luer connector 239. This is typically done after confirming blood backflow (return) from the sheath lumen 206. The female luer connector 257 is configured to be hydraulically coupled to a male luer connector 258 at a distal end 261 of the rotating hemostatic valve (RHV) 259. The male luer connector 258 is configured to be freely and sealingly rotatable in relation to the distal end 261 of the rotating hemostatic valve (RHV) 259. The rotating hemostatic valve (RHV) 259 further comprises a valve 260 configured for sealingly placing elongate devices through. In some embodiments, the valve 260 comprises a duckbill valve. In some embodiments, the valve 260 comprises a Touhy-Borst valve. In some embodiments, the valve 260 comprises an axially-spring-loaded open/close valve. The rotating hemostatic valve (RHV) 259 further comprises a sideport 262 comprising a female luer connector 263. The female luer connector 263 is configured to be hydraulically coupled to a male luer connector 264 at a distal end 265 of an infusion or aspiration line 266.

The length of the flexible access tube 252 is between about 10 cm and 60 cm, or between about 20 cm and about 40 cm. The length of the flexible access tube 252 provides separation of the valve 260 of the rotating hemostatic valve (RHV) 259 from the arterial area of interest for the procedure. The flexible access tube 252 typically will lie on the patient's chest. In some embodiments, the linear separation between the proximal end of the rotating hemostatic valve (RHV) 259 and the dilated puncture 202 is configured to be maintained by the flexible access tube 252 length to be about 30 cm to about 80 cm, or between about 40 cm and about 70 cm. Thus, the linear separation between the distal end 208 of the curved sheath 201, and the proximal end of the rotating hemostatic valve (RHV) 259 can also be between about 30 cm and about 80 cm, or between about 40 cm and about 70 cm. This allows the procedural location for the hands of the user over the lower neck 3 and/or torso and/or groin area of the patient 1, keeping the hands of the user/physician away from the beam of the fluoroscope, and thus substantially protected from large doses of radiation. The lower neck 3 and/or torso and/or groin areas of the patient 1 are also more stable areas for the user to provide the necessary manipulations of the valve 260 and the rotating hemostatic valve (RHV) 259, and the insertion, advancement, retraction, and removal of elongate medical devices through the valve 260 of the rotating hemostatic valve (RHV) 259. The user/physician/operator is able to stand near the patient's hip, as is commonly done in cases with traditional femoral artery access. This may be helpful, as many catheterization laboratories or other procedural rooms are set up for this type of personnel placement. In some cases, the user/physician/operator is able to stand at the patient's feet. The retrograde entry of elongate diagnostic and treatment medical devices into the right superficial temporal artery 13 optimizes the ability to access the different arteries described herein, or other arteries in this area. Furthermore, the bifurcation 9 can be avoided. This can be important in diseased bifurcations, as no catheter or device need pass the diseased area directly.

Figure 8:
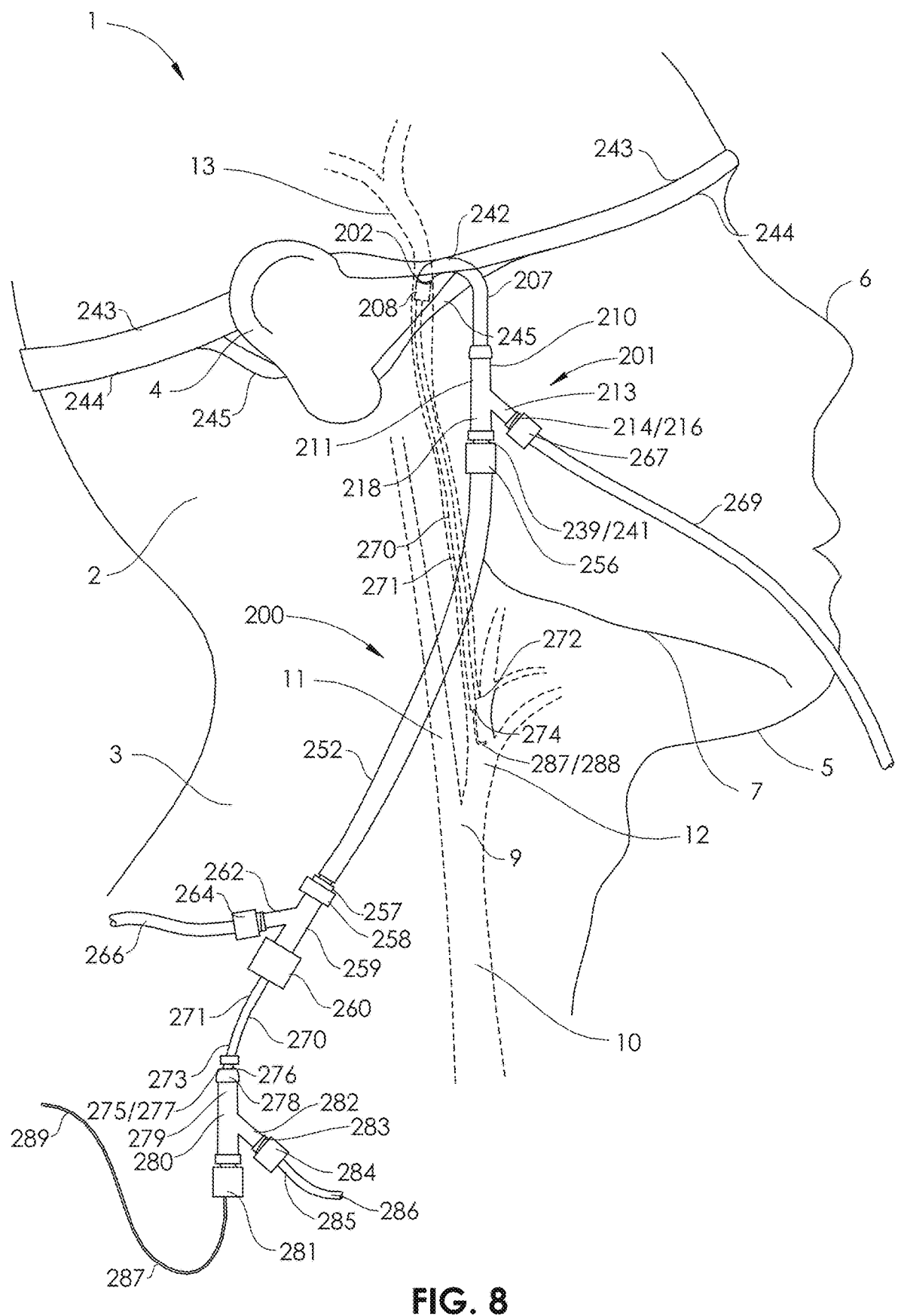
FIG. 8 is a right side view of the head of the patient illustrating a guiding catheter placed through the rotating hemostatic valve, flexible tube, and curved sheath and through the right superficial temporal artery, according to an embodiment of the present disclosure.

In FIG. 8, a user inserts a guiding catheter 270 of the access and treatment system 200 through the valve 260 of the rotating hemostatic valve (RHV) 259, through the inner lumen 253 of the flexible access tube 252, through the through lumen 212 of the connector 211, and through the lumen 206 of the shaft 207 of the curved sheath 201, and into the right superficial temporal artery 13. The guiding catheter 270 comprises an elongate shaft 271, a distal end 272, a proximal end, 273, a lumen 274, and a female luer connector 275 hydraulically coupled to the proximal end 273 and having a female luer taper 276 and a male luer lock thread 277. The guiding catheter 270 can be sized based upon the chosen intervention planned. For example, is a microcatheter is to be utilized through the guiding catheter 270, a sufficiently large enough inner lumen of the guiding catheter 270 to accommodate the placement of the microcatheter is at least about 0.022 inches or at least about 0.026 inches, or at least about 0.040 inches, or at least about 0.050 inches. A guiding catheter 270 having a sufficiently large enough inner lumen to perform procedures without a microcatheter can have an inner diameter of at least about 0.019 inches, or at least about 0.022 inches or at least about 0.026 inches, or at least about 0.040 inches, or at least about 0.050 inches.

The shaft 207 of the guiding catheter 270 can comprise a lubricious inner tubular layer ("liner") comprising a fluoropolymer such as PTFE (polytetrafluoroethylene), FEP (fluorinated ethylene propylene), PFA (perfluoroalkoxy alkane), ETFE (ethylene tetrafluoroethylene), or ECTFE (ethylene chlorotriflouroethylene). The shaft 207 can further comprise a tubular braid layer for reinforcement and torqueability, if needed, and/or a helical coil reinforcement layer, and/or a laser-machined hypo tube skeleton. The materials of these structures can comprise metallic materials such as stainless steel. An outer portion of the shaft 207 can comprise a tubular body structure comprising a polymer, such as polyurethane, polyamide, or polyether block amide. Some or all of the distal end 272 can comprise a soft tip, for example comprising a lower flexural modulus than the rest of the shaft 207, and can also be absent of any metallic reinforcement layer. The softer tip protects the inner wall of the artery during canalization and positioning. In some embodiments, the materials of at least the inner surfaces of the female luer taper 276 and the lumen 274 are non-dissolvable in dimethyl-sulfoxide (DMSO).

The female luer connector 275 is configured to be hydraulically coupled to a male luer connector 278 at a distal end 279 of another rotating hemostatic valve (RHV) 280. The male luer connector 278 is configured to be freely and sealingly rotatable in relation to the distal end 279 of the rotating hemostatic valve (RHV) 280. The rotating hemostatic valve (RHV) 280 further comprises a valve 281 configured for sealingly placing elongate devices through. In some embodiments, the valve 281 comprises a duckbill valve. In some embodiments, the valve 281 comprises a Touhy-Borst valve. In some embodiments, the valve 281 comprises an axially-spring-loaded open/close valve. The rotating hemostatic valve (RHV) 280 further comprises a sideport 282 comprising a female luer connector 283. The female luer connector 283 is configured to be hydraulically coupled to a male luer connector 284 at a distal end 285 of an infusion or aspiration line 286. The valve 281 of the rotating hemostatic valve (RHV) 280 is configured to accommodate the insertion, advancement, retraction, and removal of elongate medical devices through the rotating hemostatic valve (RHV) 280, for example, guidewires, microcatheters, flow-directed catheters, dilation catheters, stenting catheters, occlusion balloon catheters, and others.

Figure 9:
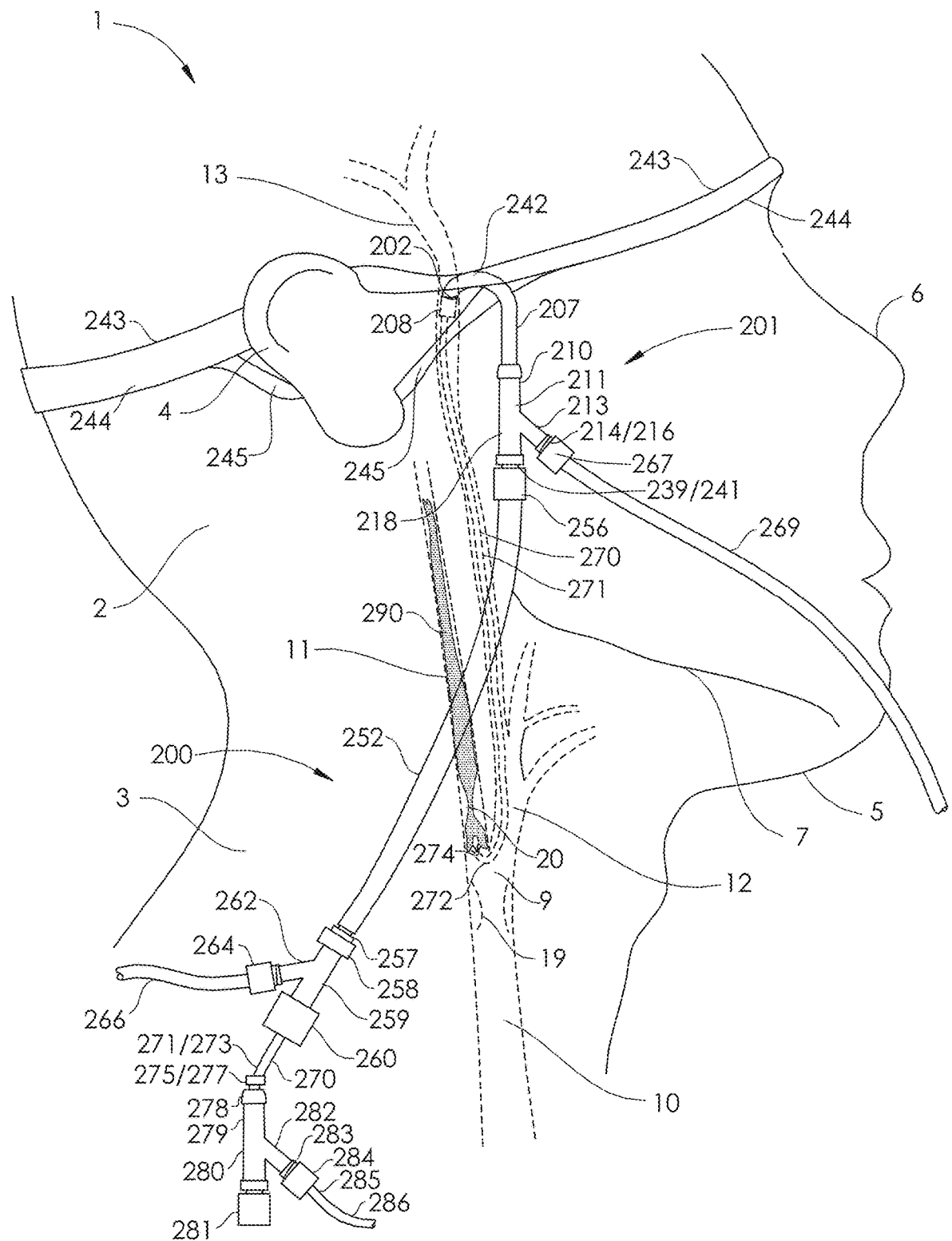
FIG. 9 is a right side view of the head of the patient illustrating angiography or fluoroscopy of a portion of the right internal carotid artery with the guiding catheter, according to an embodiment of the present disclosure.

The access and treatment system 200 facilitates retrograde access to the superficial temporal artery 13, which makes access to the external carotid artery 12, internal carotid artery 11, and their branches significantly safer and easier. In FIG. 8, the distal end 272 of the guiding catheter 270 is advanced retrogradely over a guidewire 287 through the right superficial temporal artery 13 to a location within the right external carotid artery 12, distal to the right bifurcation 9. A distal end 288 of the guidewire 287 is a curved or J-tip, and is utilized for selecting desired arteries branching from the external carotid artery 12. Alternatively, as shown in FIG. 9, the distal end 288 of the guidewire 287 has been utilized for traversing the right bifurcation 9 to reach the start of the right internal carotid artery 11, while avoiding a diseased portion 19 (e.g., atherosclerotic plaque and/or thrombus) of the right common carotid artery 10. This avoidance can be desirable whether there is also disease in the right internal carotid artery 11 and/or the right superficial temporal artery 13, or not. A proximal end 289 of the guidewire 287 is used to manipulate the guidewire 287 longitudinally/axially and to apply torque for steering. A guidewire torquer (not shown) can be attached to the proximal end 289 of the guidewire 287 to facilitate streeting.

In FIG. 9, the distal end 272 of the guiding catheter 270 has been oriented for providing an angiographic or fluoroscopic image of the right internal carotid artery 11, without disrupting any known or unknown diseased portion 19 of the right common carotid artery 10. The guidewire 287 can be removed to increase the total cross-sectional internal open area in the lumen 274 of the guiding catheter 270. Contrast media (dilute or non-dilute) is then directed through the lumen 274 of the guiding catheter 270 via a hand or powered injection via the infusion (or aspiration) line 286. The valve 281 of the rotating hemostatic valve (RHV) 280 provides a seal to assure that substantially all of the contrast media (dilute or non-dilute) is directed through the lumen 274 and into the right internal carotid artery 11. As illustrated in FIG. 9, the contrast injection and angiography or fluoroscopy 290 has indicated that there is a diseased portion 20 within the proximal right internal carotid artery 11.

Figure 10:
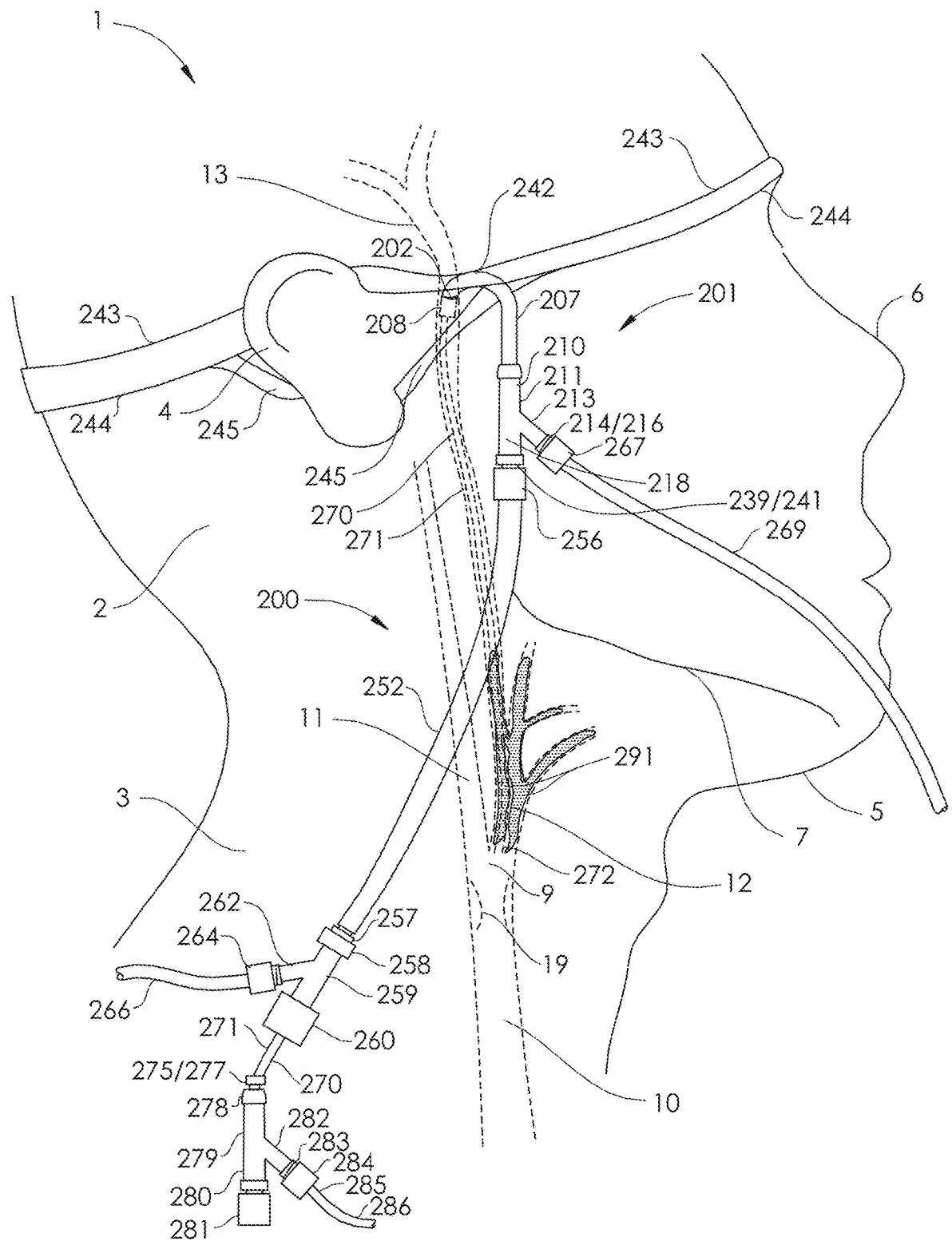
FIG. 10 is a right side view of the head of the patient illustrating angiography or fluoroscopy of a portion of the right external carotid artery with the guiding catheter, according to an embodiment of the present disclosure.

As shown in FIG. 10, the distal end 272 of the guiding catheter 270 has been advanced to a position distal to the right bifurcation 9, but at or adjacent a proximal portion of the right external carotid artery 12. In some cases, this position can be achieved initially by tacking the guiding catheter 270 over the guidewire 289 of FIG. In other cases, for example after the angiography or fluoroscopy of FIG. 9 has been completed, the guiding catheter 270 can be slightly retracted to place the distal end 272 in the position shown in FIG. 10, and the angiography or fluoroscopy of FIG. 10 can be performed. As before, contrast media (dilute or non-dilute) is directed through the lumen 274 of the guiding catheter 270 via a hand or powered injection via the infusion (or aspiration) line 286. As illustrated in FIG. 10, the contrast injection and angiography or fluoroscopy 291 has mapped the particular anatomy of the external arterial system in a portion of the right side of the outer head of the patient 1. This mapping provides information to strategize interventional cases in particular portions of this vasculature, as will be illustrated in the following figures and description.

Figure 11:
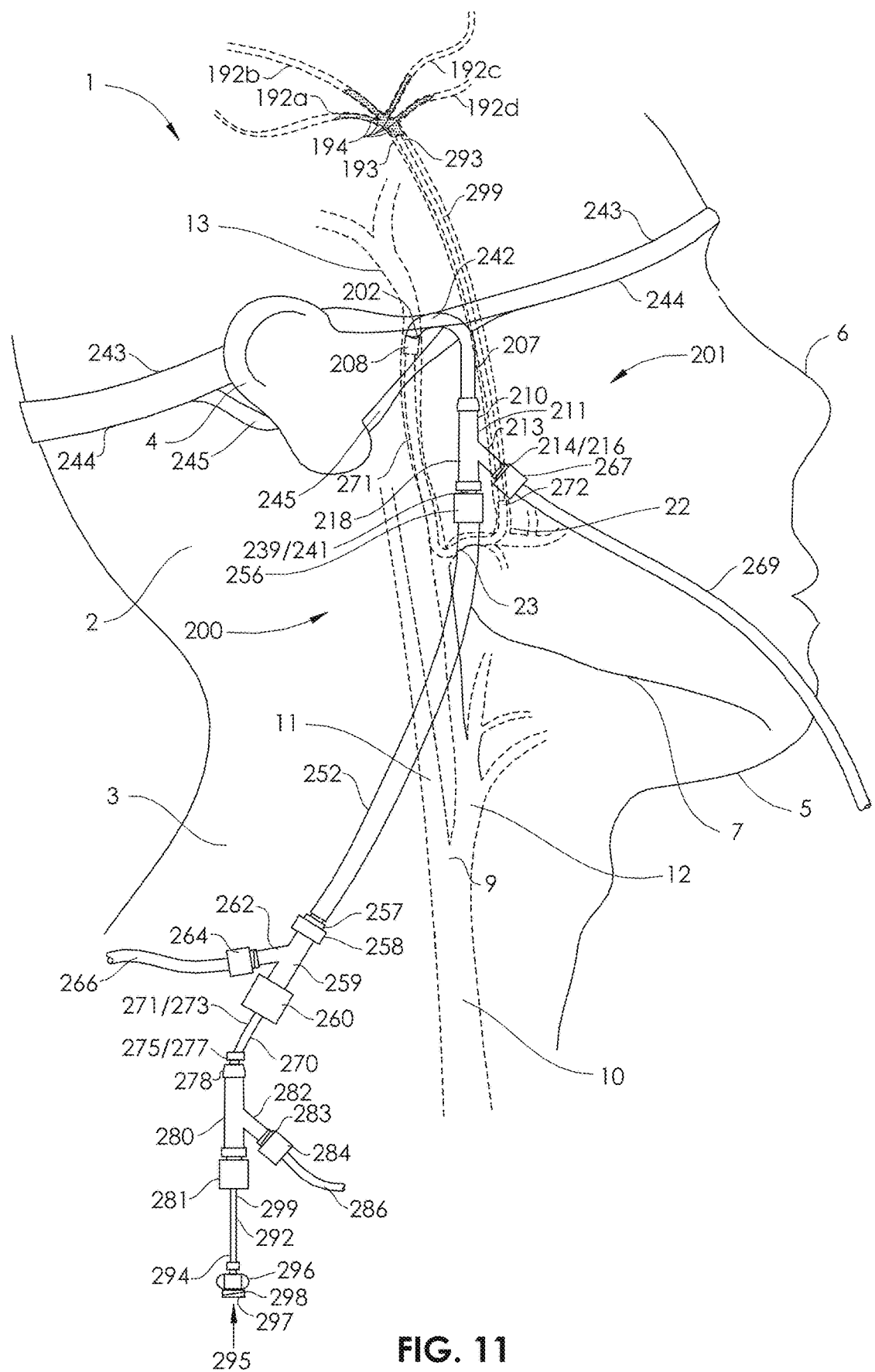
FIG. 11 is a right side view of the head of the patient illustrating embolization of the right middle meningeal artery with the a microcatheter placed through the guiding catheter, according to an embodiment of the present disclosure.

FIG. 11 illustrates an interventional procedure in a patient having a chronic subdural hematoma 21. The procedure further utilizes a microcatheter 292 of the access and treatment system 200. The microcatheter 292 has a distal end 293, a proximal end 294 a lumen 295, and a female luer connector 296 having a female luer taper 297 and a male luer lock thread 298. The microcatheter 292 comprises a shaft 299 that can comprise a lubricious inner tubular layer ("liner") comprising a fluoropolymer such as PTFE (polytetrafluoroethylene), FEP (fluorinated ethylene propylene), PFA (perfluoroalkoxy alkane), ETFE (ethylene tetrafluoroethylene), or ECTFE (ethylene chlorotriflouroethylene). The shaft 299 can further comprise a tubular braid layer for reinforcement and torqueability, if needed, and/or a helical coil reinforcement layer, and/or a laser-machined hypo tube skeleton. The materials of these structures can comprise metallic materials such as stainless steel. An outer portion of the shaft 299 can comprise a tubular body structure comprising a polymer, such as polyurethane, polyamide, or polyether block amide. Some or all of the distal end 293 can comprise a soft tip, for example comprising a lower flexural modulus than the rest of the shaft 299, and can also be absent of any metallic reinforcement layer. The softer tip protects the inner wall of the artery during canalization and positioning. In some embodiments, the materials of at least the inner surfaces of the female luer taper 297 and the lumen 295 are non-dissolvable in dimethyl-sulfoxide (DMSO).

The interventional procedure of FIG. 11 utilizes the embolization of the right middle meningeal artery (rMMA) 22, which is accessed via the right superficial temporal artery 13 and the right internal maxillary artery (rIMAX) 23. The guiding catheter 270 is retrogradely advanced through the right superficial temporal artery 13 and the antegradely into the right internal maxillary artery (rIMAX) 23. This gives support to the microcatheter 292. The distal end 293 of the microcatheter 292 is then advanced antegradely deeply into the right middle meningeal artery (rMMA) 22. A separate guidewire (not shown) can also be used through the lumen 295 of the microcatheter 292 to aid the tracking the microcatheter 292. The guidewire can then be removed from the lumen 295 after the distal end 293 reaches its desired location 193, distal in the right middle meningeal artery (rMMA) 22. An embolic material such as one or more embolic coils 194 is/are then introduced through the lumen 295 of the microcatheter 292 and into the right middle meningeal artery (rMMA) 22 to embolize the right middle meningeal artery (rMMA) 22, and/or some arteries 192a-d that branch from it. In other cases, the embolic material alternatively or additionally comprises a hardenable or curable liquid material such as an ethylene vinyl-alcohol copolymer (EVOH) dissolved in dimethyl-sulfoxide (DMSO), with a radiopaque power such as tantalum. In other cases, the embolic material alternatively or additionally comprises a hardenable or curable liquid material such as cyanoacrylate.

Figure 12:
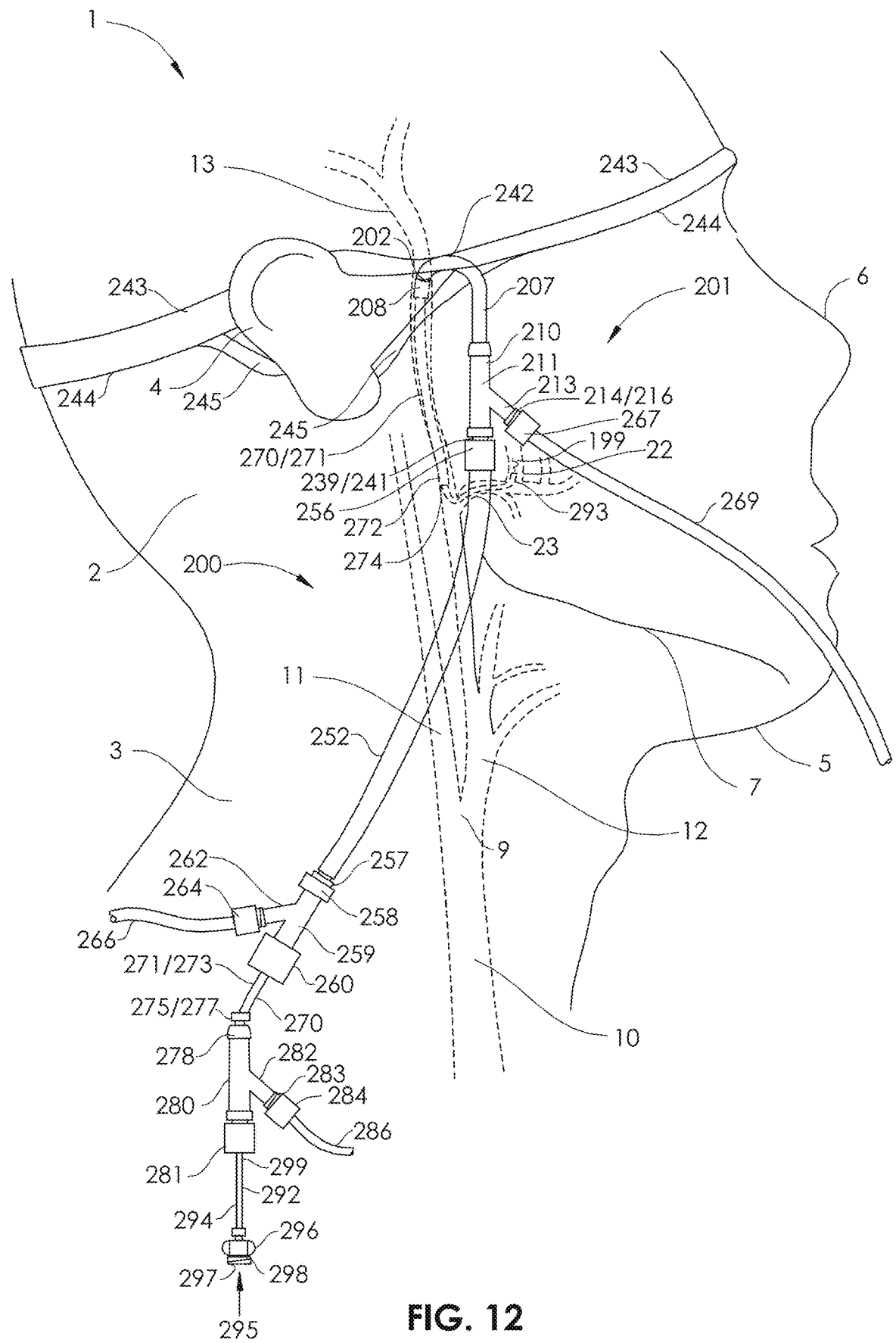
FIG. 12 is a right side view of the head of the patient illustrating infusion therapy of the right middle meningeal artery with a microcatheter placed through the guiding catheter, according to an embodiment of the present disclosure.

FIG. 12 illustrates an interventional procedure in a patient suffering from chronic migraines. The procedure utilizes the microcatheter 292 of the access and treatment system 200. The interventional procedure of FIG. 12 utilizes the delivery of a pharmacologic material into the right middle meningeal artery (rMMA) 22, which is accessed via the right superficial temporal artery 13 and the right internal maxillary artery (rIMAX) 23, as previously described in relation to FIG. 11. A separate guidewire (not shown) can also be used through the lumen 295 of the microcatheter 292 to aid the tracking the microcatheter 292. The guidewire can then be removed from the lumen 295 after the distal end 293 reaches its desired location. Lidocaine 199 is then introduced through the lumen 295 of the microcatheter 292 (e.g., using a syringe coupled to the female luer connector 296) and into the right middle meningeal artery (rMMA) 22 to treat the chronic migraines of the patient. The distal end 273 of the microcatheter 292 can be delivered into the main trunk of the right middle meningeal artery (rMMA) 22.

In some embodiments, the microcatheter 292 utilized can be a 0.021" guidewire-compatible microcatheter. The curved sheath 201 and other components can be sized accordingly to accommodate this size of microcatheter. They can each be as small as possible, for example, to accommodate the 0.021" guidewire-compatible microcatheter without having to accommodate larger microcatheters. Furthermore, they would not necessarily need to be as robust as if they were required to support a microcatheter that needed to track into branches of the internal maxillary artery (rIMAX) 23. Thus, their wall thicknesses, construction, and outer diameters can be smaller and not require as much backup support, for this application in which the distal end 273 of the microcatheter 292 only needs to be delivered into the main trunk of the internal maxillary artery (rIMAX) 23. The angle between the superficial temporal artery 13 and the internal maxillary artery (IMAX) 23 can be backwards facing, at times. If delivering devices from an antegrade entry into the external carotid artery 12 (as shown in FIG. 2), the devices (e.g., a microcatheter delivered over a guidewire) would be prone to herniating proximally into the main external carotid artery 12 trunk, during distal navigation. The access and treatment system 200 is one solution to this challenge. Alternatively, the sheath 101 of FIG. 2 can have a set curved shape (e.g., J-shape or even a Simmons catheter shape).

Figure 13:
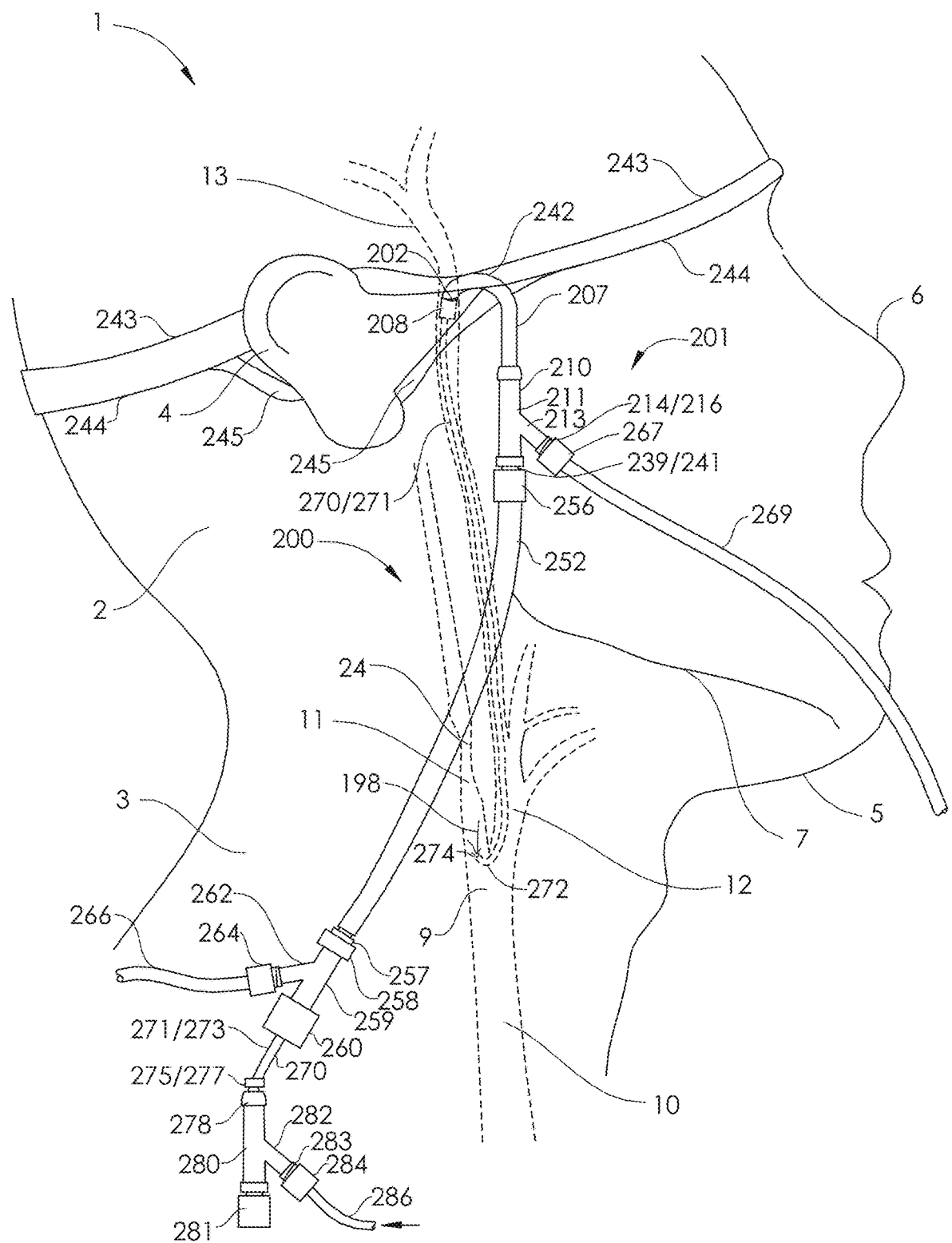
FIG. 13 is a right side view of the head of the patient illustrating pharmacological treatment of a vasospasm of the right internal carotid artery with the guiding catheter, according to an embodiment of the present disclosure.

FIG. 13 illustrates an interventional procedure in a patient suffering from vasospasm 24 of the right internal carotid artery 11. The distal end 272 of the guiding catheter 270 is tracked by the user/physician to the takeoff of the right internal carotid artery 11, for example with the help of the guidewire 287 (or even the microcatheter 292, with or without its guidewire). A drug/pharmacologic 198 is then directed through the lumen 274 of the guiding catheter 270 and into the right internal carotid artery 11 via a hand or controlled (e.g., syringe pump or infusion pump) injection via the infusion (or aspiration) line 286. In some cases, the pharmacologic 198 comprise one or more of: a calcium channel blocker (such as nimodipine), an antiplatelet agent, a corticosteroid, an anticoagulate, a nitrate, a beta-blocker, a vasodilator, an alpha-1-blocker, stellate ganglion block, phenytoin, valproate, diazepam, edaravone, intranasal dihydroergotamine (DHE), midodrine, fludrocortisone, and/or gabapentin. Additionally or alternatively, one or more dilation balloon can be inserted through the lumen 274 and deployed (expanded) within the right internal carotid artery 11 at the location of the vasospasm 24. Additionally or alternatively, one or more carotid stent can be inserted through the lumen 274 and deployed (expanded) within the right internal carotid artery 11 at the location of the vasospasm 24. In other cases, the microcatheter 292 can be inserted through the lumen 274 of the guiding catheter 270 and into the right internal carotid artery 11, and the injection of the pharmacologic 198 can be performed through the lumen 295 of the microcatheter 292.

Figure 14:
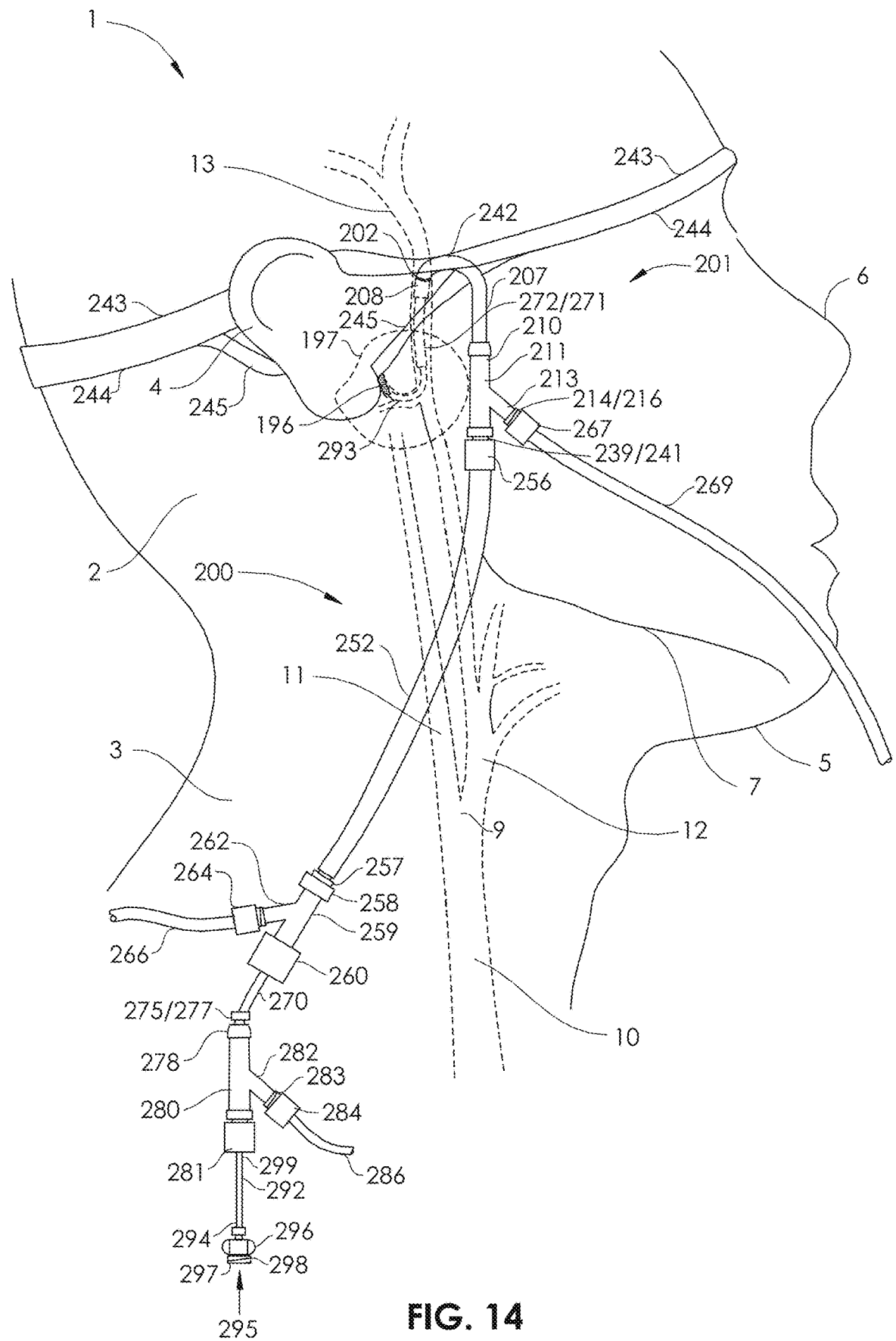
FIG. 14 is a right side view of the head of the patient illustrating embolization of a meningioma with a microcatheter placed through the guiding catheter, according to an embodiment of the present disclosure.

FIG. 14 illustrates an interventional procedure in a patient having a meningioma 197 that is intended to later be removed via a surgical procedure. It is often desirable to embolize some, most, or all of the significant arteries feeding the meningioma 197. The procedure of FIG. 14 performs pre-operative embolization of the meningioma 197 utilized the systems and techniques described herein. The distal end 272 of the guiding catheter 270 is tracked by the user/physician to a location near the main arterial trunk or entry point to the meningioma 197. The microcatheter 292 is then tracked through the lumen 274 of the guiding catheter 270 to one or more arterial locations 196 at or within the meningioma 197, one at a time. In each location, an embolic material such as EVOH dissolved in DMSO is then introduced through the lumen 295 of the microcatheter 292 and into the one or more feeding arteries, to significantly, or sufficiently for operative purposes, embolize the meningioma 197. In addition to meningiomas 197, other tumors can be treated, for example other neoplasms.

The access and treatment system 200 can be utilized for superficial temporal artery 13 based access in treatment of a number of maladies, including but not limited to: embolization of arteriovenous malformations (AVMs), embolization of AV fistulae, thrombolytic treatment, clot/thrombus retrieval, treatment of vasospasm, and delivery of other intravascular devices.

Figure 15:
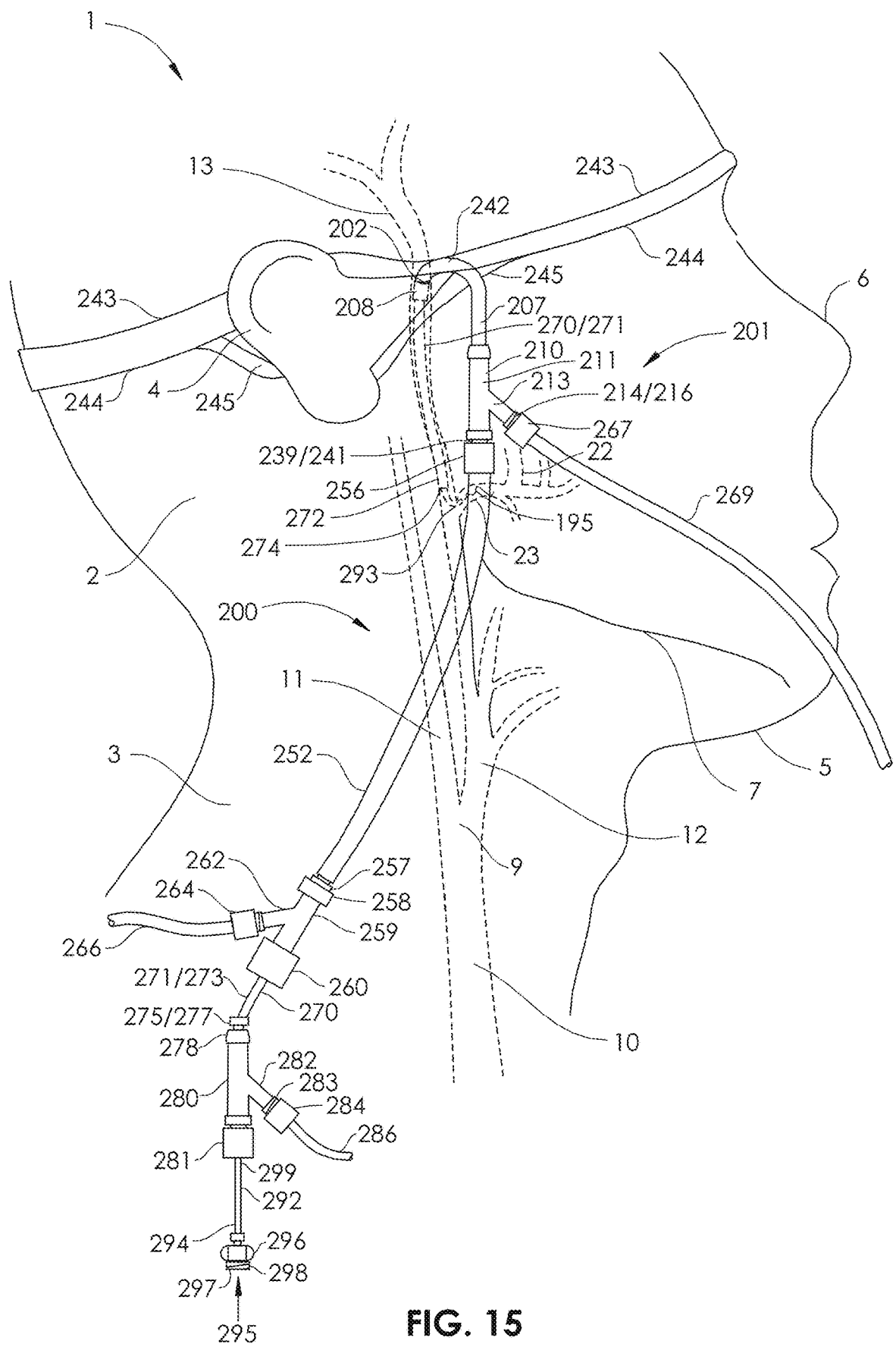
FIG. 15 is a right side view of the head of the patient illustrating embolization of the right internal maxillary artery with a microcatheter placed through the guiding catheter, according to an embodiment of the present disclosure.

FIG. 15 illustrates an interventional procedure in a patient having one or more of: epistaxis (nosebleed), nasopharygeal angioma, and/or a head and neck cancer. In these patients is may become desired to embolize an internal maxillary artery (IMAX) 23 utilizing the systems and techniques described herein, as shown in FIG. 15. The interventional procedure of FIG. 15 utilizes the embolization of the right internal maxillary artery (rIMAX) 23, which is accessed via the right superficial temporal artery 13. The guiding catheter 270 is retrogradely advanced through the right superficial temporal artery 13 until that its distal end 272 is at the takeoff of the right internal maxillary artery (rIMAX) 23, or actually entering the right internal maxillary artery (rIMAX) 23. This gives support to the microcatheter 292. The distal end 293 of the microcatheter 292 is then advanced antegradely into the right internal maxillary artery (rIMAX) 23. A separate guidewire (not shown) can also be used through the lumen 295 of the microcatheter 292 to aid the tracking the microcatheter 292. The guidewire can then be removed from the lumen 295 after the distal end 293 reaches its desired location. An embolic material such as one or more embolic coils 195 are then introduced through the lumen 295 of the microcatheter 292 and into the right internal maxillary artery (rIMAX) 23 to embolize the right internal maxillary artery (rIMAX) 23. In other cases, the embolic material alternatively or additionally comprises a hardenable or curable liquid material such as an ethylene vinyl-alcohol copolymer (EVOH) dissolved in dimethyl-sulfoxide (DMSO), with a radiopaque power such as tantalum. In other cases, the embolic material alternatively or additionally comprises a hardenable or curable liquid material such as cyanoacrylate.

Figure 16:
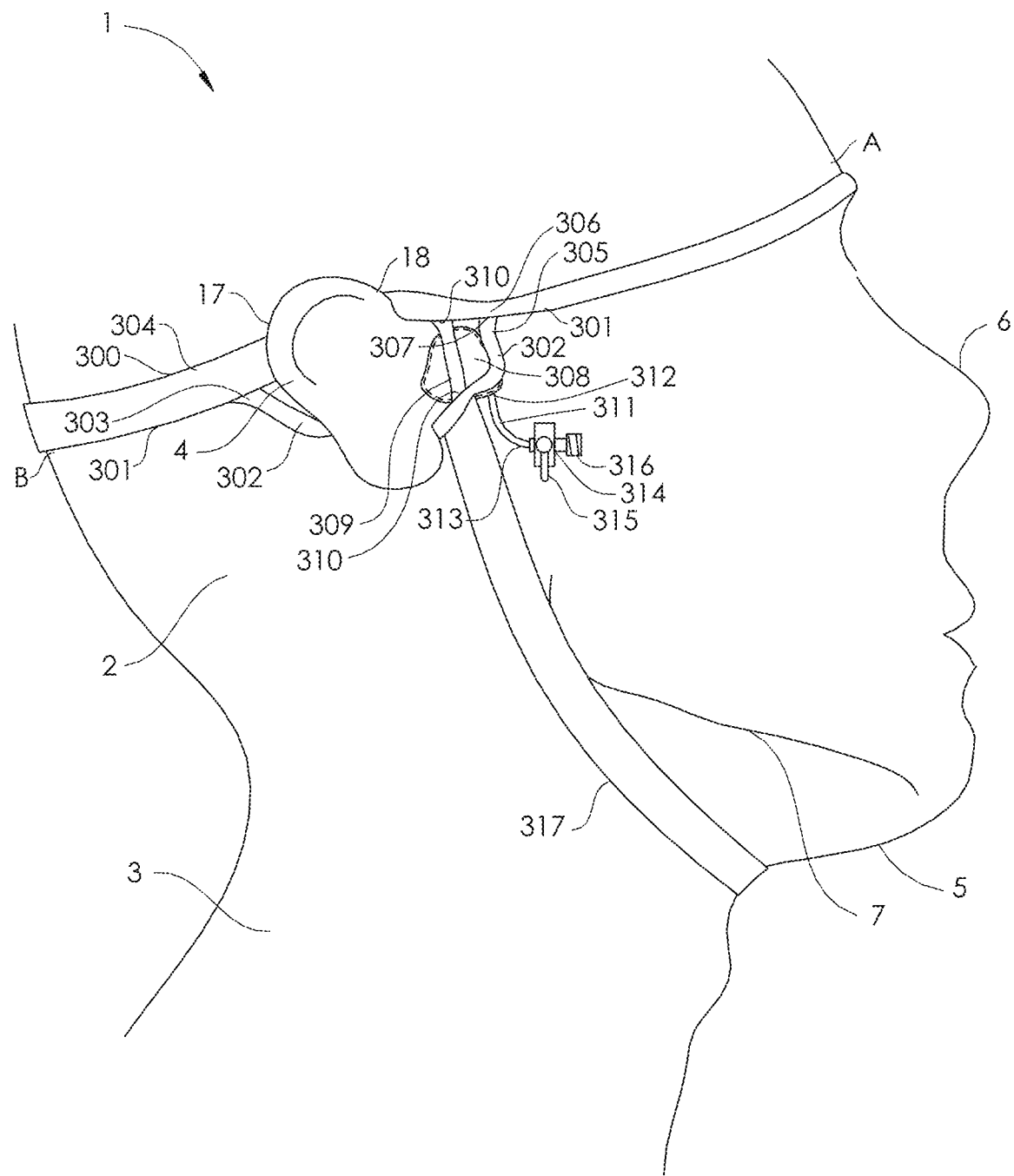
FIG. 16 is a right side view of the head of the patient illustrating a head band or strap with a compression element in place, according to an embodiment of the present disclosure.

Following any one of the interventional procedures described herein, it may be desired to increase the speed of hemostasis after the elements of the system 100, 200 are pulled out and removed from the patient 1. Turning to FIG. 16, a hemostasis band 300 comprising a continuous elastic head band 301 that is generally biased to a circumference that is less than a circumference of the head 2 of the patient 1 that extends around the head 2 of the patient 1 and traverses a point A and a point B. Point A is slightly above an eyebrow of the patient 1 and point B is at the back of the head 2 toward the top of the occipital bone. The circumference of the elastic head band 301 is configured to be stretched, causing an increasing bias caused by elastic material within the elastic head band 301, and reaching an increased diameter that is greater than the circumference of the head 2 of the patient 1 that extends around the head 2 of the patient 1 and traverses point A and point B. In alternative embodiments, the elastic head band 301, instead of being continuous, comprises an elastic or non-elastic linear, non-continuous band that can be tied to a desired circumference and/or amount of tightness around the head 2 of the patient 1 that extends around the head 2 of the patient 1 and traverses point A and point B. In other embodiments, a Velcro® (hook and loop) closure can be utilized.

The elastic head band 301 (or other band) acts a base structure. To this base structure, an ear loop 302 is secured. The ear loop 302 can comprise an elastic or non-elastic band, or a string or rope. The ear loop 302 in some embodiments comprises polymeric tape. A first end 303 of the ear loop 302 secures to a rear portion 304 of the elastic head band 301 that is configured to be located at or adjacent the posterior 17 of the ear 4 of the patient 1. A second end 305 of the ear loop 302 secures to a forward portion 306 of the elastic head band 301 that is configured to be located at or adjacent the anterior 18 of the ear 4 of the patient 1. The elastic head band 301 and the ear loop 302 can be thermally bonded to each other, or connected via sewing, stapling, adhesive, epoxy, or hot melt 307. An inflatable balloon 308 is held under the ear loop 302, at a portion anterior to the ear 4, and an additional support 309 extends around the inflatable balloon 308, while allowing space for balloon 308 to expand. Alternatively, the additional support 309 comprises an elastic band that is able to stretch and increase its length while the balloon 308 expands, and the support 309 continues to cradle the balloon 308. The additional support 309 is secured to the elastic head band 301 and to the ear loop 302, for example with an adhesive, epoxy, or hot melt 310. Thus, the elastic head band 301 is configured to hook over the ear 4, and pass behind the superior crus of the ear and at least partially below the superior portion of the helix, while the ear loop 245 is configured to pass substantially below the ear 4. In the configuration shown in FIG. 16, the ear loop 302 also hooks underneath the ear lobe, though this is not a requirement, as ear lobes tend to have a variety of morphologies. The ear loop 302 in cooperation with the elastic head band 301 provide stability of the securement band 300 on the head 2 of the patient 1. The securement band 301 is maintained circumferential by one or both ears 4.

The balloon 308 comprises a semi-compliant material such as polyvinyl chloride, polyurethane, polyamide, polyethylene, or other polyolefins. In some embodiments, if there is enough support (e.g., comprising multiple supports 309 or even a mesh or web), the balloon 308 can comprise a more compliant material, such as a silicone or natural rubber material. In some embodiments, the balloon 308 comprises a contoured substantially non-compliant material such as a polyester. An inflation tube 311 is hydraulically coupled at a first end 312 to an interior of the balloon 308 and extends therefrom. A second end 313 of the inflation tube 311 is hydraulically coupled to a valve 314, comprising an on/off handle 315 and a female luer lock connector 316. A syringe full of air, other gases, water, saline, or other liquids can be hydraulically coupled to the female luer lock connector 316, the valve can be opened, and the balloon 308 can be inflated to a desired volume and/or pressure that, when supported by the elastic head band 301, the ear loop 302, and the one or more supports 309, applies a surface pressure against the dilated puncture 202, including both the skin and the arterial wall. In addition, an under-the-neck support 317 is connected between the ear loop 302 (on the treatment side) and the elastic head band 301 (on the contralateral side), and provides further securement, providing a tight, firm, seating of the hemostasis band 300 between the location where the top of the ear 4 meets the head 2 and underneath the chin 5. Because of the dynamic size nature provided by the balloon 308, the hemostasis band 300 can be a one-size-fits-all device, that is tailored to the size of the head 2 of the patient 1 by the inflation of the balloon 308. However, multiple sizes pf the hemostasis band 300 are possible.

The internal pressure/volume can be adjusted at any time by medical personnel, or by the recovering patient or their support members, to provide more or less surface pressure against the dilated puncture 202. The balloon 308 allows an increased time of surface pressure application and "hands-off" maintenance. This, combined with the reversal of anticoagulant (e.g., heparin) after the procedure, accelerated the stability of the patient related to the hemostasis at the dilated puncture 202. In patients accessed via femoral artery puncture, mobility is significantly reduced during the healing of the puncture site or sites. In patients accessed via radial artery puncture, the use of one or both arms is significantly reduced during the healing of the puncture site or sites. However, with the superficial temporal artery 13 puncture 202 taught herein, or the external carotid artery puncture 102, there is little or no short-term effect on the four limbs of the patient 1. Furthermore, the dilated puncture 202 over the superficial temporal artery 13 tends to be very superficial, this making hemostasis with the balloon 308, even in a hands-off manner quite possible. In older patients, there may even be no clinical reasons to preserve the patency of the superficial temporal artery 13, and the treating physician may choose to purposely close off/occlude the superficial temporal artery 13 with an embolic agent such as EVOH or embolic coils. When the desired parameter is reached, the hemostasis band 300 can be entirely removed from the patient, and a bandage can be placed over the closed puncture 202. This parameter may comprise a certain amount of elapsed time, or a certain measurement of clotting time (e.g., ACT). The balloon 308 can be fully or substantially deflated prior to removing the hemostasis band 300 to make removal easier.

Figure 17:
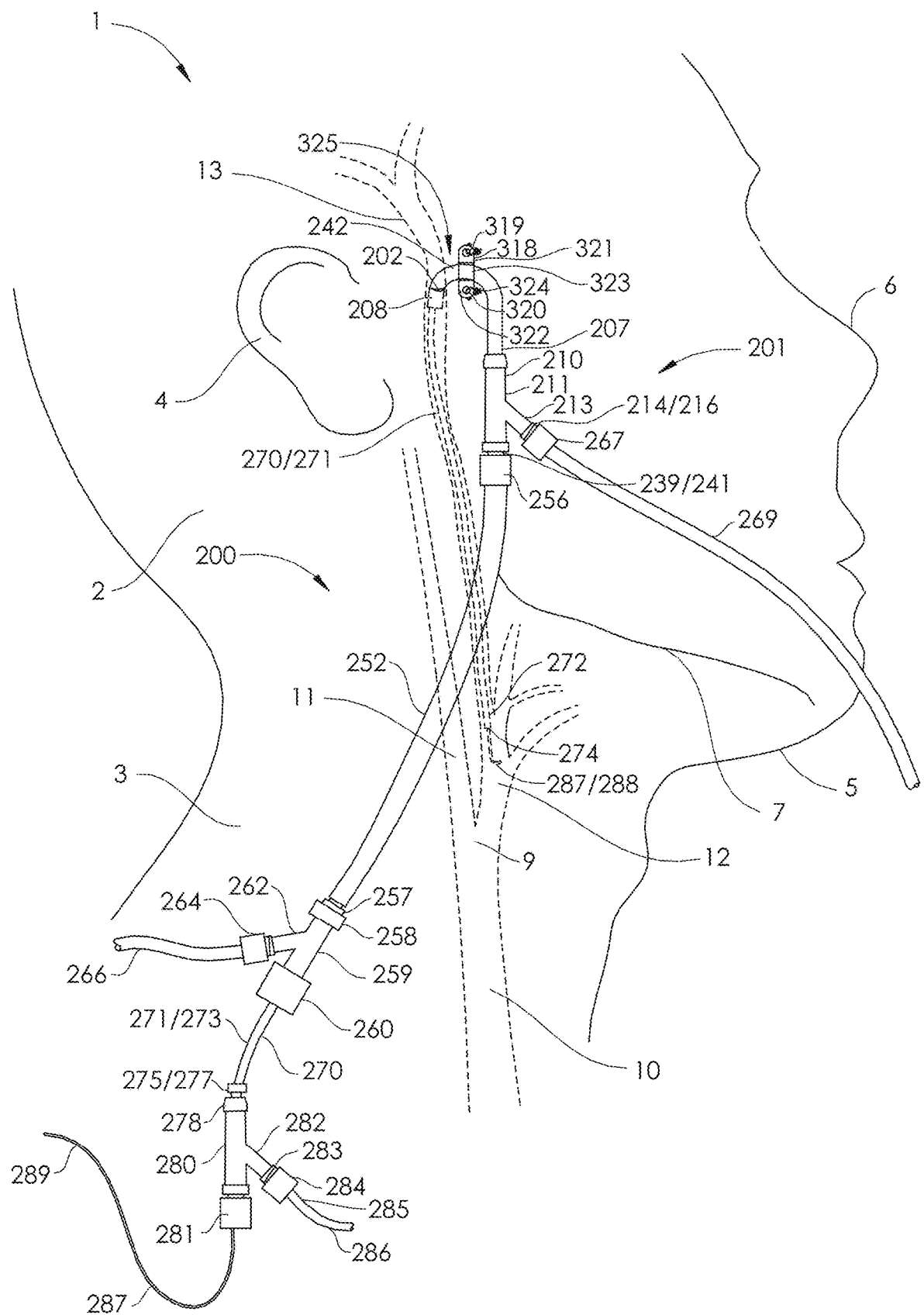
FIG. 17 is a right side view of the head of the patient illustrating an alternative securement of the curved sheath utilizing suture holes, according to an embodiment of the present disclosure.

FIG. 17 illustrates and alternative access and treatment system 200' that is identical to the access and treatment system 200, except that the securement band 243 is replaced completely by a suturable clip 318 having a first suture hole 319 and a second suture hole 320. The clip 318 comprises a first planar arm 321 having the first suture hole 319 passing therethrough and a second planar arm 322 having the second suture hole 320 passing therethrough. Extending between the two arms 321, 322 is a semi-circular curve portion 323 configured to have a bottom contour that closely covers and holds the shaft 207 of the curved sheath 201 at the U-shaped curve 242. Suture 324 is passed through the suture holes 319, 320 and the clip 318 is sutured tightly to the skin of the patient 1 at a desired location 325. Thus, the clip 318 holds the shaft 207 securely allowing very little movement of the distal end 208 of the shaft 207 and guarding against loss of canalization.

Figure 18:
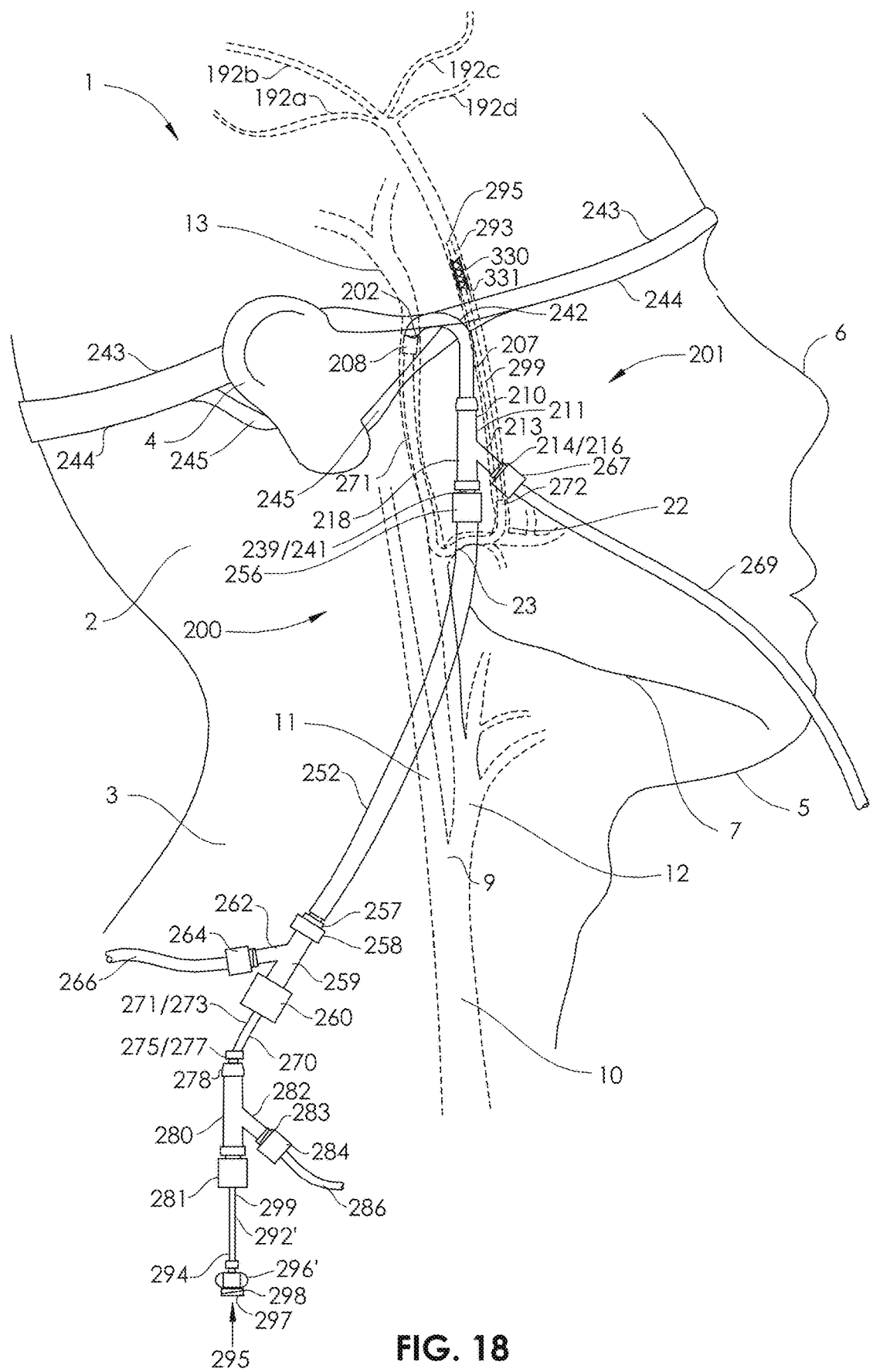
FIG. 18 is a right side view of the head of a patient illustrating a first step in implantation of an infusion microcatheter in the right middle meningeal artery, according to an embodiment of the present disclosure.
Figure 19:
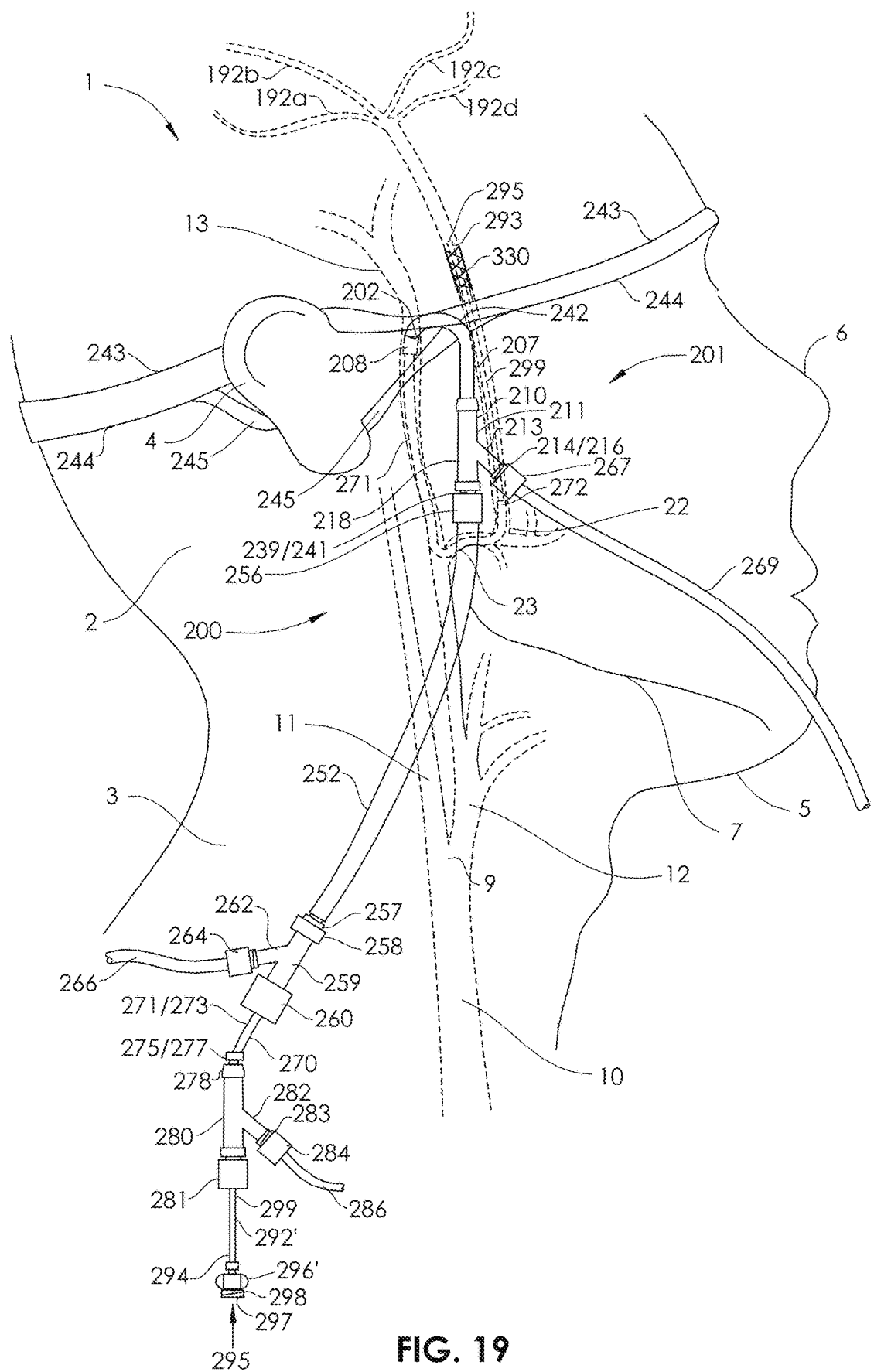
FIG. 19 is a right side view of the head of the patient illustrating a second step in implantation of the infusion microcatheter of FIG. 18 in the right middle meningeal artery, according to an embodiment of the present disclosure.

FIG. 18 illustrates an interventional procedure in a patient requiring chronic infusion in the right middle meningeal artery (rMMA) 22. The procedure follows the access procedure described in relation to the access and treatment system 200 of FIG. 11, but utilizes a microcatheter 292' configured to anchor within the right middle meningeal artery (rMMA) 22 with a stent 330, carried on the shaft 299, and at least partially secured to the shaft. The microcatheter 292' has removable female luer connector 296' having a female luer taper 297 and a male luer lock thread 298, which is removably hydraulically couplable to the shaft 299 and to the lumen 295. The stent 330 is configured to be expanded and collapsed, via a retractable recovering sheath 331. Alternatively, the sheath can be collapsed and expanded by moving the microcatheter 292' in an out of the lumen 274 of the guiding catheter 270. The stent 330 is self-expanding and comprises a superelastic alloy, such as nickel-titanium alloy. In alternative embodiments, the stent 330 comprises a shape-memory alloy that expands when exposed to elevated temperatures, for example body temperature (~37° C.) or temperatures above body temperature, by injection of heated saline. FIG. 18 illustrates the stent 330 in an unexpanded state. FIG. 19 illustrates the stent 330 in the expanded state, anchoring the distal end 296 of the microcatheter 292' to the inner wall of the right middle meningeal artery (rMMA) 22.

Figure 20:
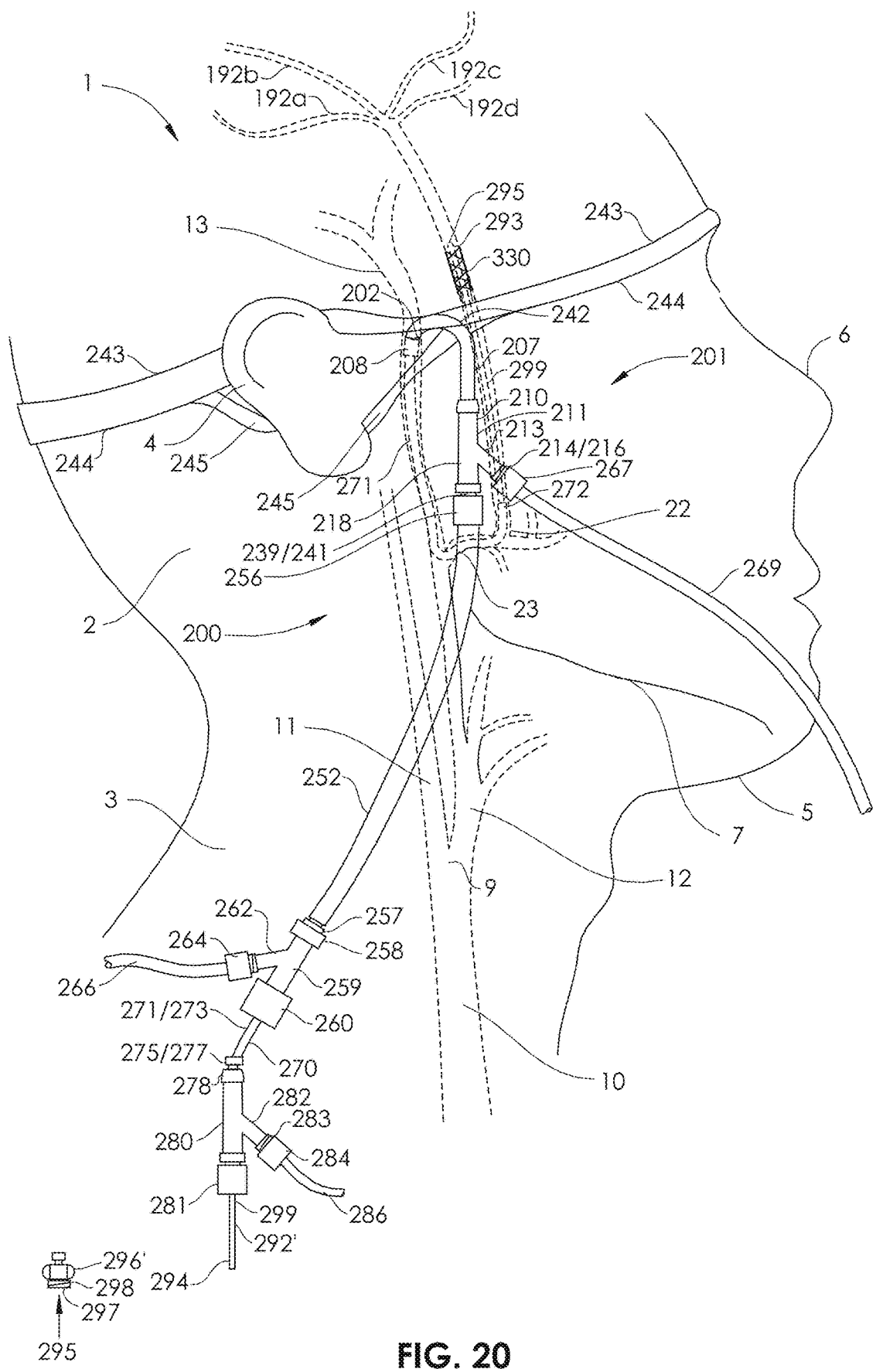
FIG. 20 is a right side view of the head of the patient illustrating a third step in implantation of the infusion microcatheter of FIG. 18 in the right middle meningeal artery, according to an embodiment of the present disclosure.

In FIG. 20, the removable female luer connector 296' is removed from the shaft 299. The lumen 295 at the proximal end 294 of the shaft 299 can be blocked to prevent any blood loss.

Figure 21:
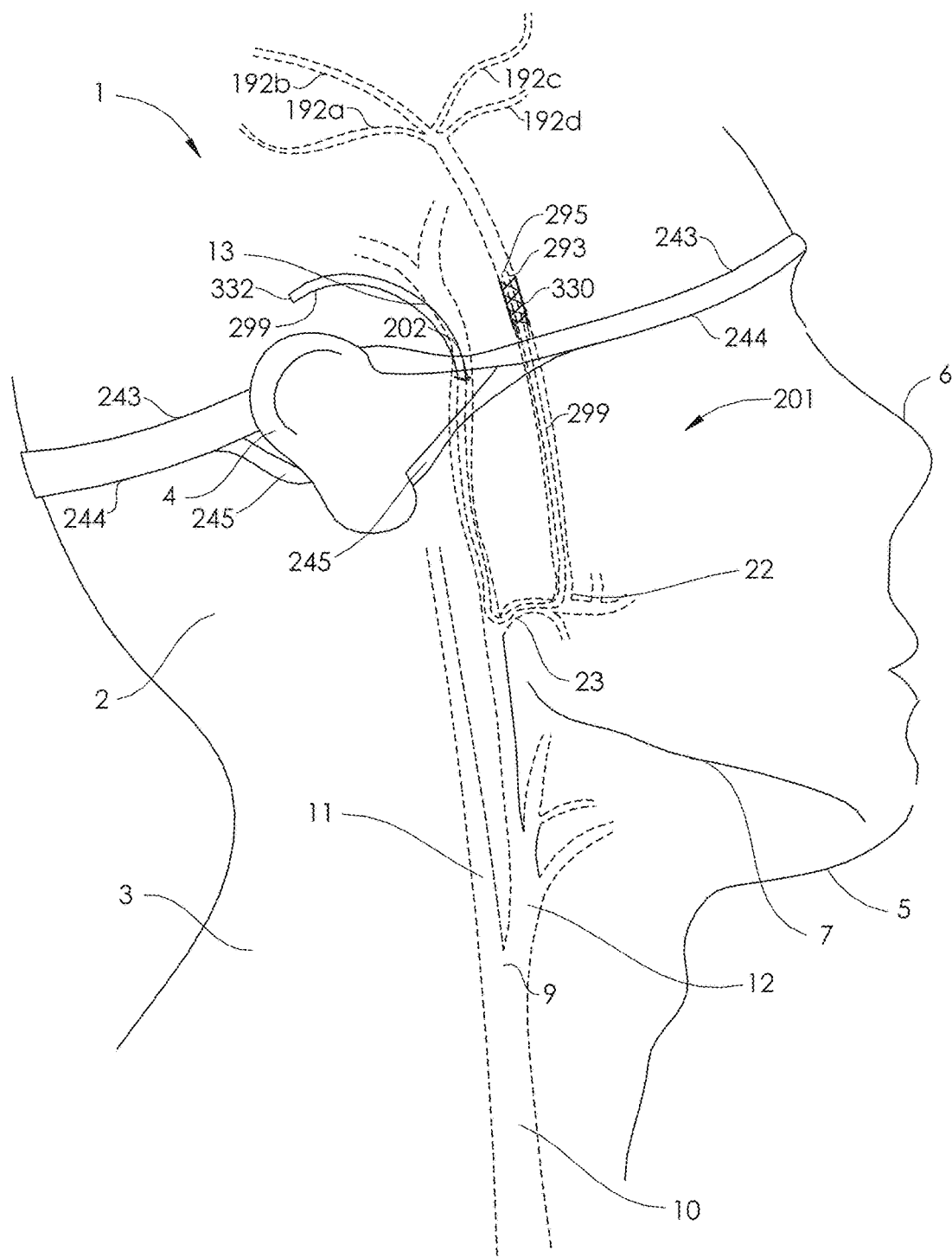
FIG. 21 is a right side view of the head of the patient illustrating a fourth step in implantation of the infusion microcatheter of FIG. 18 in the right middle meningeal artery, according to an embodiment of the present disclosure.

In FIG. 21, the shaft 299 can be trimmed to a desired length to provide a proximal connection end 332, which provides access to the proximal end of the lumen 295 and which will be hydraulically coupled to an implantable infusion reservoir and pump system 333.

Figure 22:
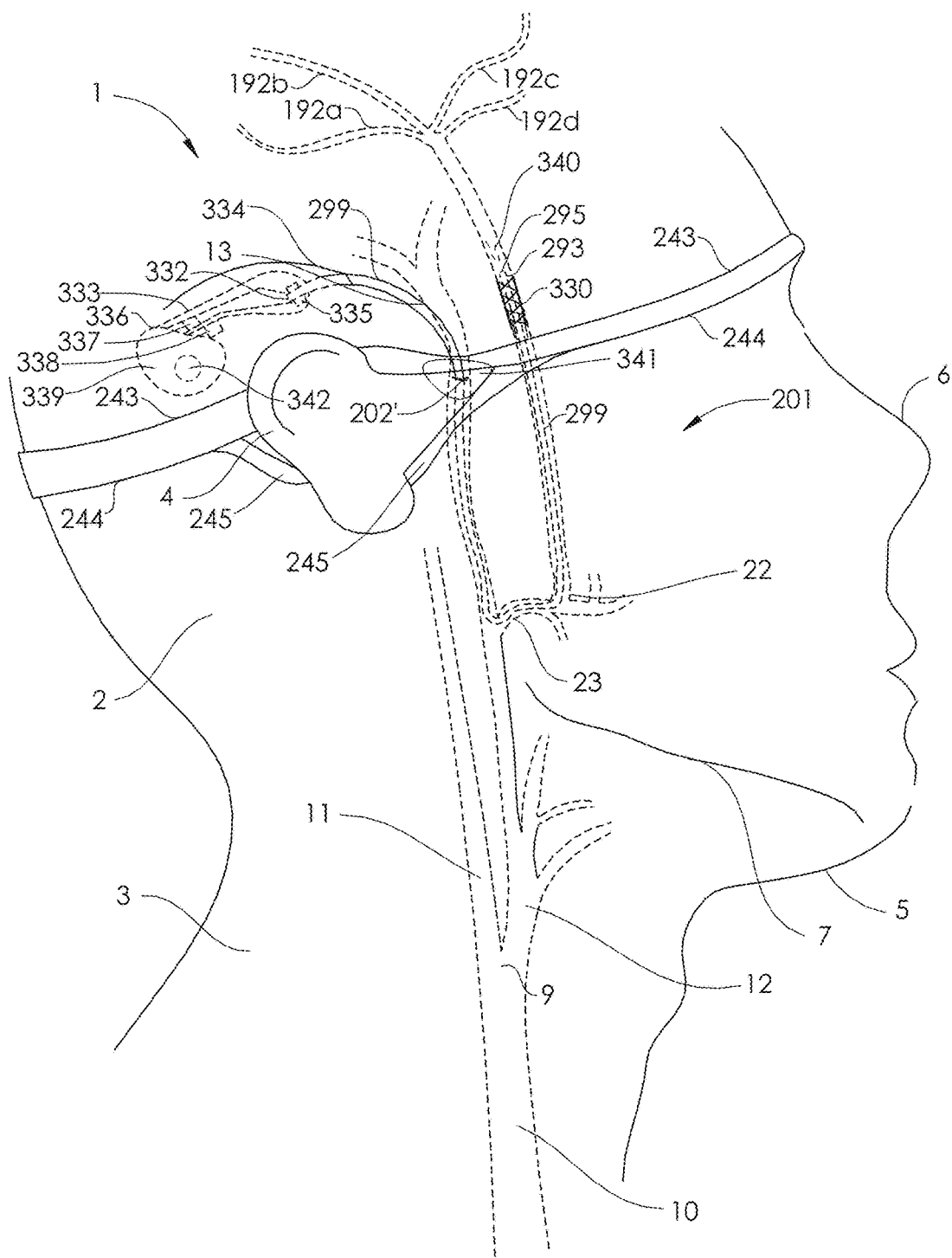
FIG. 22 is a right side view of the head of the patient illustrating a fifth and final step in implantation of the infusion microcatheter of FIG. 18 in the right middle meningeal artery, and connection of it to a drug infusion system, according to an embodiment of the present disclosure.

FIG. 22 illustrates the full implantation of the microcatheter 292' with the implantable infusion reservoir and pump system 333. An incision 334 is made over the ear of the patient 1. A tunnel is made under the skin of the patient 1, and the implantable infusion reservoir and pump system 333 is placed in the below the hairline/scalp in a location posterior to the ear 4 and slightly above the mastoid. The connection end 332 of the shaft 299 is hydraulically coupled to the interior of the housing 336 of the implantable infusion reservoir and pump system 333 by sealing the shaft 299 inside the o-ring seal 335. In some embodiments, the o-ring seal 335 can comprise a quad-ring seal, or another type of seal. An impeller 337 is powered by a controller/power board 338 to drive a medicant/drug/pharmacologic material 340 from a reservoir 339 which is coupled to the housing 336. The incision 334 is closed by suturing or cyanoacrylate, or other methods. The reservoir 339 can be periodically filled with the medicant/drug/pharmacologic material 340 by puncturing the scalp of the patient and an elastomeric access port 342 with the needle of a syringe, to fill the interior of the reservoir 339. The expanded stent 330 is secured to the distal end 293 of the microcatheter 292', and thus is held in place as the medicant/drug/pharmacologic material 340 is delivered over time out the lumen 295. The healed or healing puncture 202' is covered over with a balloon 341 or patch/bandage that is carried by the securement band 243. When the therapy has been completed, the implantable infusion reservoir and pump system 333 and microcatheter 292' are removed from the patient 1.

Figure 23:
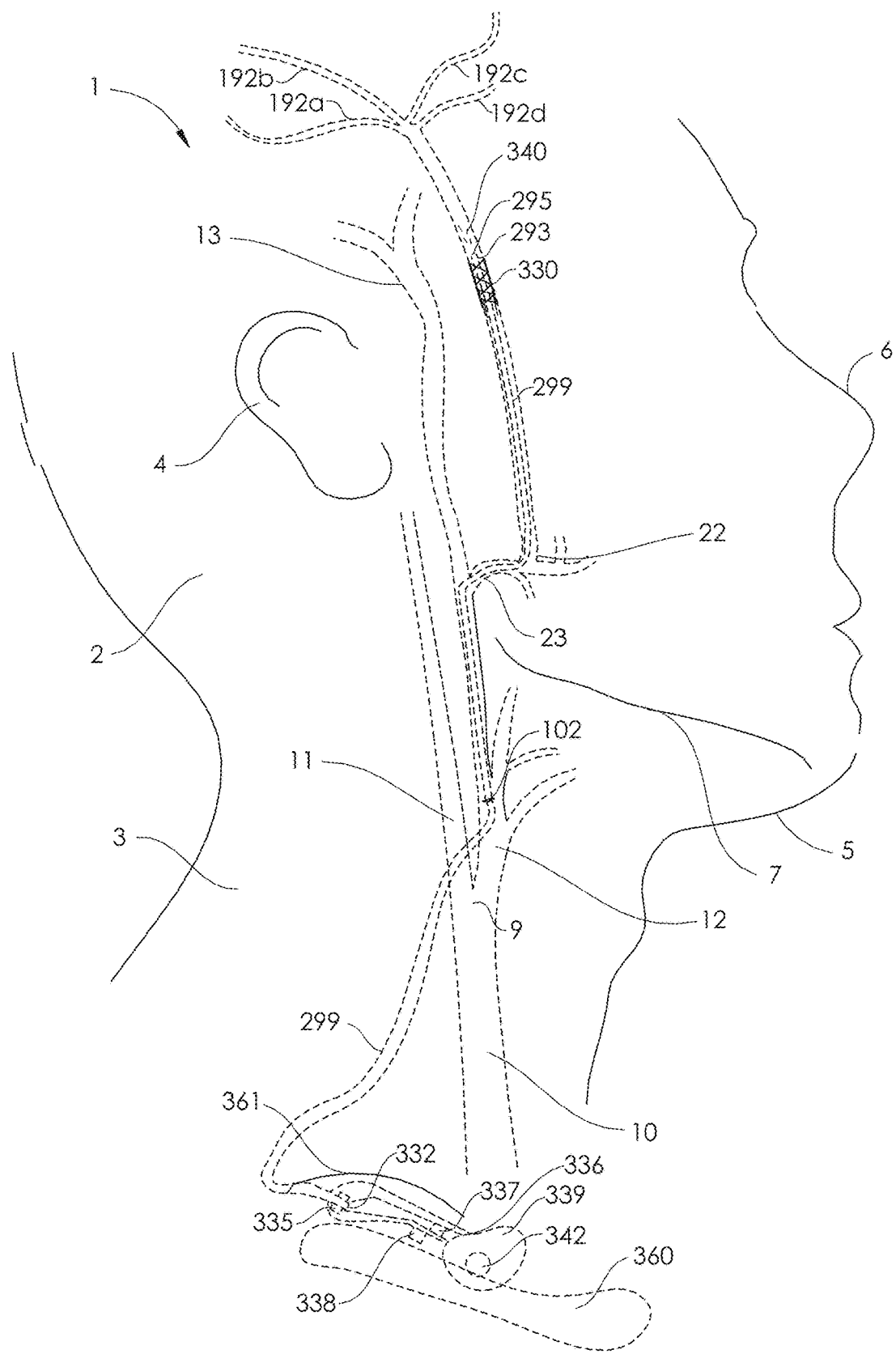
FIG. 23 is a right side view of the head and shoulder of a patient illustrating an alternative implantation configuration and method of the drug infusion system of FIG. 22, according to an embodiment of the present disclosure.

FIG. 23 illustrates the full implantation of the microcatheter 292' with the implantable infusion reservoir and pump system 333. The implantation is similar to that shown in FIG. 22, however the direct external carotid artery 12 technique of FIG. 2 has been used. An incision 361 is made over the clavicle 360 and the implantable infusion reservoir and pump system 333 is placed in a tunnel that is made under the skin above the clavicle 360. The shaft 299 extending from the puncture 102 is tunneled down the neck 2 of the patient 1. Alternatively, in either the case of FIG. 22 or the case of FIG. 23, the shaft 299 can be shortened such that it only extends slightly from the puncture 102, 202, and an extension tube can be coupled between the lumen 206 and the the implantable infusion reservoir and pump system 333.

Figure 24:
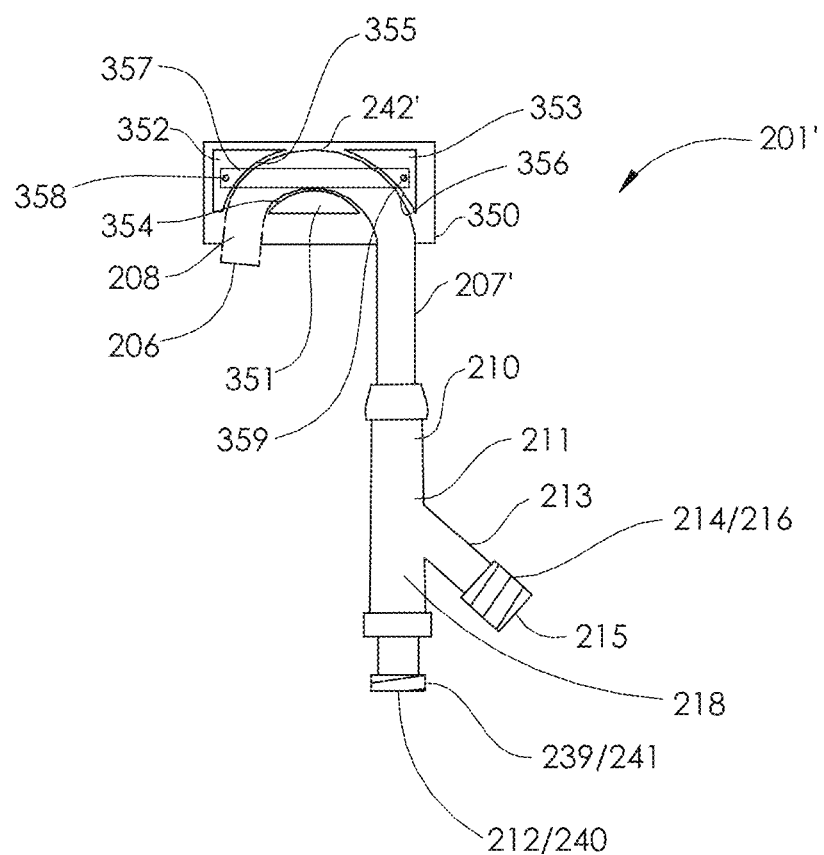
FIG. 24 is a plan view of an alternative curved sheath, according to an embodiment of the present disclosure.

FIG. 24 illustrates an alternative curved sheath 201' that comprises a straight shaft 207' that has not been precurved. Instead, the U-shaped curve 242' in the shaft 207' is provided by a shape holder 350 (or shape maintenance tool) having a flat base that can be placed, or can be adhesively attached to the patient (e.g., with a peel-away exposed adhesive backside). Attached to the plate of the shape holder 350 is a first convex curve form 351, a first concave curve form 352, and a second concave curve form 353. The curve forms 351, 352, 353 can each comprise a curved, radiused cavity 354, 355, 356 that matches the outer circular shape of the shaft 207'. The curve forms 351, 352, 353 can be close enough to each other, so that the shaft 207' can be snapped in place. In other embodiments, one or more of the curve forms 351, 352, 353 can be slidable to lock the shaft 207 curve forms 351, 352, 353 in place. As shown in FIG. 24, however, an overlayable cover sheet 357 that has a hole 359 on each side, which are configured to snap over pins 358, which are connected to an extend from opposite sides of the base of the shape holder 350. The cover sheet 357 can also be unsnappable. The components of the shape holder 350 can comprise rigid plastic, such as high-density polyethylene or polyoxymethylene, the pins 358 con comprise stainless steel or other metals, and the cover sheet 357 can comprise a polyester. The shape holder 350, when fully assembled around the shaft 207', maintains the U-shaped curve 242' in the curved sheath 201', and thus maintains the U-shape in the lumen 206 of the shaft 207'.

In some embodiments, the controller/power board 338 comprises a rechargeable battery or a capacitor that can be recharged and/or powered by inductive coupling. In some embodiments, an external remote control is configured to communicate two-way with the controller/power board 338, for example, to start, stop, or change flow rates of the pump system 333. The implantable infusion reservoir and pump system 333 enables chronic delivery of one or more medicants to some or all of the right middle meningeal artery (rMMA) 22, and arteries 192a-d that branch from it.

Figure 25:
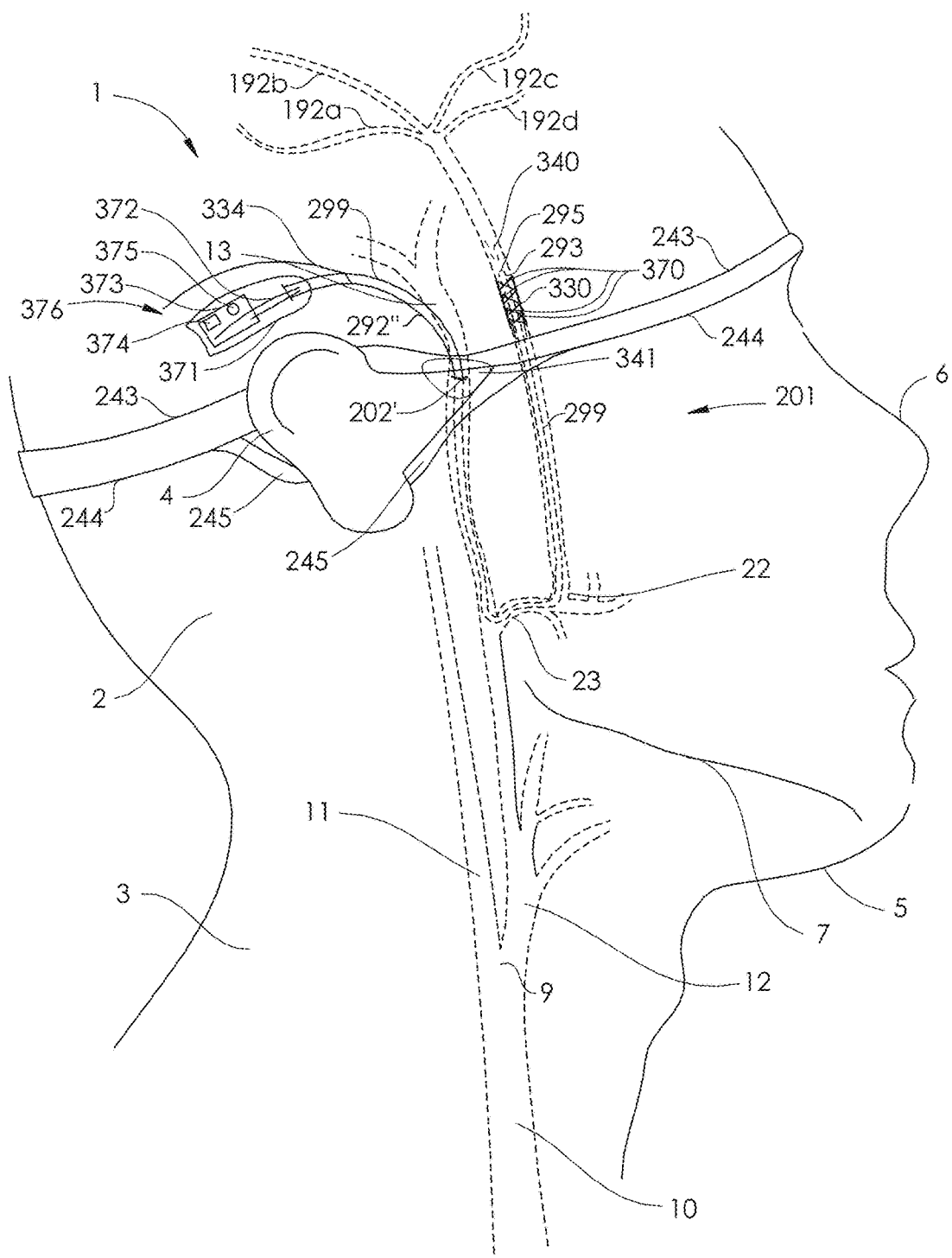
FIG. 25 is a right side view of the head and shoulder of a patient illustrating a final step in implantation of an electrical stimulation catheter in the right middle meningeal artery, and connection to an electrical stimulation system, according to an embodiment of the present disclosure.

FIG. 25 illustrates the final step of an interventional procedure performed in the right middle meningeal artery (rMMA) 22 in much the same way as the procedure illustrated in FIGS. 18-22. The procedure utilizes a microcatheter 292" that also comprises a stent 330 configured to anchor within the right middle meningeal artery (rMMA) 22. However, the microcatheter 292" includes one or more electrodes 370 carried on the stent 330, configured to contact the wall of the right middle meningeal artery (rMMA) 22 (or any other artery into which it is delivered). The electrodes 370 are electrically connected to wires 372 which extend through the microcatheter 292", either within a lumen, or embedded in the catheter tubing wall. The wires 372 couple to a circuit 373 of an electrical stimulation system 376. The circuit 373 is contained within a housing 371. The housing 371 is configured to be tunneled within the tunnel created below the incision 334. The circuit 373 also carries a controller 374 for exciting different electrodes 370 at specific times, or applying particular levels of voltage to the electrodes to energize them. A battery 375 is also carried on the circuit 373 and can comprise a disposable battery or a rechargeable battery. The circuit 373 can also be configured for inductively-coupled activation or inductive charging. A remote (not shown) can be provided to communicate (two-way) with the controller 374. The incision 334 is closed by suturing or cyanoacrylate, other methods. The securement band 243 stabilizes the microcatheter 292" for chronic use. The electrical stimulation system 376 is configured to apply stimulation to the right middle meningeal artery (rMMA) 22 over time, according to programming applied via input to the controller 374. When the therapy has been completed, the electrical stimulation system 376 and microcatheter 292" are removed from the patient 1. Alternatively, the electrical stimulation system 376 can be implanted in the direct external carotid artery method shown in FIG. 23.

The following clauses include examples of apparatus and methods of the disclosure.

Clause 1: In one example, a system for accessing one or more artery in a head and neck area of a patient without traversing any portion of the aortic arch of the patient includes an access sheath having a shaft having a distal end and a proximal end and a sheath lumen extending therethrough, the distal end of the shaft configured for placement through a puncture in skin of a subject and retrogradely into a superficial temporal artery of the subject, the shaft having a length of between about 1 cm and about 6 cm, or in some examples between about 1.5 cm and about 5 cm, or in some examples between about 2 cm and about 4 cm, the system further including a curved intermediate tubular junction having an inner lumen extending therethrough, the inner lumen having a distal end that is hydraulically coupled to the sheath lumen of the access sheath and a proximal end, the curved intermediate tubular junction having a curve configured to maintain itself during use to have a curve angle of between about 90° and about 270°, the system further including a resilient access-extension tube having an extension lumen extending therethrough, the extension lumen having a distal end and a proximal end, the distal end of the extension lumen hydraulically coupled to the proximal end of the inner lumen of the curved intermediate tubular junction, an insertion portion of the access-extension tube spaced from the distal end of the extension lumen and configured to allow insertion of an elongate medical device into the extension lumen for advancement through the extension lumen, the inner lumen, and the sheath lumen, and into the arterial system of the subject.

Clause 2: In some examples, the system includes clause 1, and further includes an imager configured for identifying a target artery for puncture.

Clause 3: In some examples, the system includes clause 2, wherein the imager does not utilize ionizing radiation.

Clause 4: In some examples, the system includes clause 3, wherein the imager utilizes ultrasound.

Clause 5: In some examples, the system includes clause 4, wherein the ultrasound is configured to operate at a frequency of between about 5 MHz and about 15 MHz.

Clause 6: In some examples, the system includes any one of clauses 2-5, wherein the imager has a field of view (FOV) of between about 5 cm and about 35 cm.

Clause 7: In some examples, the system includes any one of clauses 1-6, wherein the access-extension tube further includes a hemostasis portion configured to seal around the elongate medical device to limit loss of arterial blood from the subject.

Clause 8: In some examples, the system includes clause 7, wherein the insertion portion and the hemostasis portion of the access-extension tube are both provided by a hemostatic valve.

Clause 9: In some examples, the system includes clause 8, wherein the hemostatic valve includes a rotating hemostatic valve (RHV).

Clause 10: In some examples, the system includes either one of clauses 8-9, wherein the hemostatic valve includes a user-openable-and-closable valve configured to allow insertion and advancement of the elongate medical device and the sealing around the elongate medical device.

Clause 10: In some examples, the system includes clause 10, wherein the user-openable-and-closable valve is a Touhy-Borst.

Clause 11: In some examples, the system includes clause 10, wherein the user-openable-and-closable valve is a spring-loaded, axially-actuatable valve.

Clause 12: In some examples, the system includes any one of clauses 1-11, wherein the access sheath further includes a female luer connector at a proximal end of the access sheath, the female luer connector hydraulically coupled to the sheath lumen.

Clause 13: In some examples, the system includes clause 12, wherein the curved intermediate tubular junction further includes a male luer connector hydraulically coupled to the distal end of the inner lumen, the male luer connector configured to be hydraulically coupled to and decoupled from the female luer connector of the access sheath.

Clause 14: In some examples, the system includes clause 13, wherein the system further includes a dilator having an outer diameter, a dilating tip and a dilator lumen therethrough, the dilator configured to be inserted through the sheath lumen such that the dilating tip extends distally of the distal end of the shaft of the access sheath, and wherein the outer diameter of the dilator is sized to provide mechanical support to the shaft of the access sheath.

Clause 15: In some examples, the system includes clause 14, wherein the system further includes a guidewire configured for placement through the dilator lumen of the dilator.

Clause 16: In some examples, the system includes clause 15, wherein the system further includes a needle having a needle lumen, the needle lumen configured for placement of the guidewire.

Clause 17: In some examples, the system includes any one of clauses 1-16, wherein the access-extension tube is permanently attached to the curved intermediate tubular junction.

Clause 18: In some examples, the system includes clause 17, wherein a distal portion of the access-extension tube is bonded to a proximal portion of the curved intermediate tubular junction.

Clause 19: In some examples, the system includes clause 18, wherein the distal portion of the access-extension tube is bonded to the proximal portion of the curved intermediate tubular junction by a thermal bond.

Clause 20: In some examples, the system includes clause 18, wherein the distal portion of the access-extension tube is bonded to the proximal portion of the curved intermediate tubular junction by an adhesive bond.

Clause 21: In some examples, the system includes clause 18, wherein the distal portion of the access-extension tube is bonded to the proximal portion of the curved intermediate tubular junction by an epoxy bond.

Clause 22: In some examples, the system includes clause 18, wherein the distal portion of the access-extension tube is bonded to the proximal portion of the curved intermediate tubular junction by a solvent-activated bond.

Clause 23: In some examples, the system includes any one of clauses 1-16, wherein the curved intermediate tubular junction further includes a first luer connector at a proximal end of the curved intermediate tubular junction, the first luer connector hydraulically coupled to the inner lumen, the first luer connector further having a first internal lumen configured for the elongate medical device to be passed therethrough.

Clause 24: In some examples, the system includes clause 23, wherein the access-extension tube further includes a second luer connector at a distal end of the access-extension tube, the second luer connector hydraulically coupled to the extension lumen, the second luer connector further having a second internal lumen configured for the elongate medical device to be passed therethrough, wherein the second luer connector is configured to be hydraulically coupled to and decoupled from the first luer connector.

Clause 25: In some examples, the system includes any one of clauses 1-24, wherein the sheath lumen of the access sheath is sized such that the elongate medical device can have a maximum diameter at large as 4F.

Clause 26: In some examples, the system includes clause 25, wherein the inner lumen of the curved intermediate tubular junction and the extension lumen of the access-extension tube are each sized such that the elongate medical device can have a maximum diameter at large as 4F.

Clause 27: In some examples, the system includes any one of clauses 1-26, wherein the curve of the curved intermediate tubular junction includes a U-shape portion.

Clause 28: In some examples, the system includes clause 27, wherein the U-shape portion is substantially rigid.

Clause 29: In some examples, the system includes any one of clauses 1-28, wherein at least a distal 4 cm of the shaft of the access sheath is configured to be retrogradely placed into the superficial temporal artery.

Clause 30: In some examples, the system includes any one of clauses 1-28, wherein at least a distal 3 cm of the shaft of the access sheath is configured to be retrogradely placed into the superficial temporal artery.

Clause 31: In some examples, the system includes any one of clauses 1-28, wherein at least a distal 2 cm of the shaft of the access sheath is configured to be retrogradely placed into the superficial temporal artery.

Clause 32: In some examples, the system includes any one of clauses 1-31, wherein the elongate medical device includes a guiding catheter.

Clause 33: In some examples, the system includes any one of clauses 1-32, wherein the system further includes a microcatheter configured to be inserted through a lumen of the elongate medical device.

Clause 34: In some examples, the system includes clause 33, wherein the microcatheter has an effective inner diameter of 0.021 inch or less.

Clause 35: In some examples, the system includes clause 33, wherein the microcatheter has an effective inner diameter of 0.017 inch or less.

Clause 36: In some examples, the system includes any one of clauses 1-35, wherein the elongate medical device is capable of being advanced into a middle meningeal artery via the system.

Clause 37: In some examples, the system includes any one of clauses 1-36, wherein a proximal portion of the access sheath includes one or more suture holes configured for suturing the access sheath to skin of the subject.

Clause 38: In some examples, the system includes clause 37, wherein the one or more suture holes are configured for suturing the access sheath to one or more additional layers of the scalp, besides the skin.

Clause 39: In some examples, the system includes any one of clauses 1-32, wherein the elongate medical device includes a microcatheter.

Clause 40: In some examples, the system includes clause 39, wherein the microcatheter has an effective inner diameter of 0.021 inch or less.

Clause 41: In some examples, the system includes clause 39, wherein the microcatheter has an effective inner diameter of 0.017 inch or less.

Clause 42: In one example, a system for accessing one or more arteries in a head and neck area of a patient includes an access sheath including a tubular shaft having a distal end and a proximal end and a sheath lumen extending therethrough, the distal end of the shaft configured for placement through a puncture in skin and an adjacent arterial wall of a superficial temporal artery of a subject and to extend retrogradely within a portion of the superficial temporal artery of the subject, the proximal end of the shaft including a first connection portion, an intermediate portion of the sheath located between the distal end of the shaft and the proximal end of the shaft, the intermediate portion forming a curved shape of the sheath lumen, a resilient access-extension tube having an extension lumen extending therethrough, the extension lumen having a distal end and a proximal end, the distal end of the extension lumen configured to hydraulically couple to the sheath lumen at the first connection portion, and sealable opening carried by the access-extension tube and spaced from the distal end of the extension lumen, the sealable opening configured to allow insertion of an elongate medical device into the extension lumen for advancement through the extension lumen when the access-extension tube is coupled to the access sheath, for passage through the extension tube and the sheath lumen, and into the superficial temporal artery of the subject.

Clause 43: In one example, a method for accessing one or more artery in a head and neck area of a patient includes creating an opening in skin an in an adjacent arterial wall of a superficial temporal artery of a subject, inserting through the opening a distal end of a tubular shaft of an access sheath, the shaft further including a proximal end including a first connection portion, and a sheath lumen extending therethrough, the sheath including an intermediate portion located between the distal end of the shaft and the proximal end of the shaft, the intermediate portion forming a substantially U-shape or J-shape of the sheath lumen, adjusting the shaft such that the distal end extends retrogradely within a portion of the superficial temporal artery of the subject, hydraulically coupling a distal end of an extension lumen of a resilient access-extension tube to the first connection portion, the extension lumen further including a proximal end, the extension lumen extending through the access-extension tube, the access extension tube further carrying a sealable opening, inserting an elongate medical device through the sealable opening and into the extension lumen and advancing the device through the extension lumen and the sheath lumen, and advancing the medical device retrogradely through at least a portion of the superficial temporal artery of the subject, and performing a medical procedure with the elongate medical device within the arterial system of the subject.

Clause 44: In one example, a method for performing a therapeutic procedure in a patient includes placing a distal end of a sheath into a superficial temporal artery of a subject, advancing an elongate medical device through a lumen of the sheath and retrogradely within a portion of the superficial temporal artery of the subject, anchoring a portion of the elongate medical device in place to an artery of the subject selected from the list consisting of: the superficial temporal artery, an internal maxillary artery, a middle meningeal artery, and a branch of middle meningeal artery, and performing a procedure over at least 24 hours.

Clause 45: In some examples, the method includes clause 45, wherein the procedure includes a diagnostic procedure.

Clause 46: In some examples, the method includes clause 45, wherein the procedure includes a therapeutic procedure.

Clause 47: In some examples, the method includes clause 46, wherein the therapeutic procedure includes delivering a medicant within the vasculature of the subject.

Clause 48: In some examples, the method includes clause 46, wherein the therapeutic procedure includes applying electrical stimulation within the vasculature of the subject.

Clause 49: In some examples, the method includes any one of clauses 44-49, wherein the portion of elongate medical device includes a stent-like anchor configured to expand against an inner arterial wall.

Clause 50: In some examples, the method includes any one of clauses 44-49, wherein the method further includes attaching a proximal control to the elongate medical device, creating an incision near one of an ear or a clavicle of the subject, creating a tunnel under the skin of the subject from the incision, placing the proximal control within the tunnel, and closing the incision.

Clause 51: In one example, a system for facilitating healing after removal from a patient of one or more interventional devices that were previously placed through a direct puncture or one or both superficial temporal arteries of the patient includes a band configured to surround a head of a subject, the band having an outer surface and an inner surface opposite the outer surface, a first expandable member carried within the inner surface and configured to be placed over a first puncture site of a first superficial temporal artery of the subject, the first expandable member having a non-expanded state and an expanded state, and a control for moving the first expandable member from its non-expanded state toward its expanded state.

Clause 52: In one example, the system includes clause 51, wherein the expandable member is an inflatable member.

Clause 53: In one example, the system includes either one of clauses 51-52, wherein the control is further configured to move the first expandable member toward its non-expanded state.

Clause 54: In one example, the system includes any one of clauses 51-53, wherein the band further includes a closure portion configured to open the band into a linear configuration and to lock the band closed into a circular configuration.

Clause 55: In one example, the system includes clause 54, wherein the closure portion includes a multiple hook-and-loop attachment.

Clause 56: In one example, the system includes clause 54, wherein the closure portion includes an adhesive attachment.

Clause 57: In one example, the system includes clause 54, wherein the band has an adjustable circumference.

Clause 58: In one example, the system includes any one of clauses 51-57, wherein the band includes an anterior portion configured to be located on the nose bridge of the subject.

Clause 59: In one example, the system includes any one of clauses 51-58, wherein the system further includes a second expandable member carried within the inner surface and configured to be placed over a second puncture site of a second superficial temporal artery of the subject, the second puncture site contra-lateral to the first puncture site on the subject's head, the second expandable member having a non-expanded state and an expanded state, wherein the control if further configured for simultaneously moving the first expandable member and the second expandable member from their non-expanded states toward their expanded states.

Clause 60: In one example, the system includes clause 59, wherein the control is configured to simultaneously inject a non-compressible liquid into the first expandable member and the second expandable member.

Clause 61: In one example, a method of accessing one or more artery in a head and neck area of a patient without traversing any portion of the aortic arch of the patient includes puncturing the skin of a subject adjacent a first superficial temporal artery, inserting a first access sheath retrogradely into the first superficial artery, the access sheath including a shaft having a distal end and proximal end and a sheath lumen extending therethrough, the shaft having a length of 8 cm or less, providing a curved intermediate tubular junction and a resilient access-extension tube, wherein the curved intermediate tubular junction has an inner lumen extending therethrough, the inner lumen having a distal end that configured to be hydraulically coupled to the sheath lumen of the access sheath and a proximal end, the curved intermediate tubular junction having a curve configured to maintain itself during use to have a curve angle of between about 90° and about 270°, the access-extension tube having an extension lumen extending therethrough, the extension lumen having a distal end and a proximal end, the distal end of the extension lumen configured to be hydraulically coupled to the proximal end of the inner lumen of the curved intermediate tubular junction, an insertion portion of the access-extension tube spaced from the distal end of the extension lumen and configured to allow insertion of an elongate medical device into the extension lumen for advancement through the extension lumen, the inner lumen, and the sheath lumen, and into the arterial system of the subject, coupling the distal end of the inner lumen of the curved intermediate tubular junction to the sheath lumen of the access sheath, coupling the distal end of the extension lumen to the proximal end of the inner lumen of the curved intermediate tubular junction, and inserting an elongate medical device through the insertion portion, the extension lumen, the inner lumen, and the sheath lumen, and into the arterial system of the subject.

Clause 62: In one example, the method includes clause 61, wherein inserting the first access sheath includes inserting the distal end of the shaft between about 2 cm and about 4 cm into the first superficial artery.

Clause 63: In one example, the method includes either one of clauses 61-62, wherein the method further includes performing a procedure with the elongate medical device.

Clause 64: In one example, the method includes either one of clauses 61-62, wherein the elongate medical device includes a guiding catheter having a guiding catheter lumen, and therein the method further includes inserting a microcatheter through the guiding catheter lumen and into the arterial system of the subject.

Clause 65: In one example, the method includes clause 64, wherein the method further includes performing a procedure through a microcatheter lumen of the microcatheter.

Clause 66: In one example, the method includes either one of clauses 63 or 65, wherein the procedure includes a diagnostic procedure.

Clause 67: In one example, the method includes either one of clauses 63 or 65, wherein the procedure includes a therapeutic procedure.

Clause 68: In one example, the method includes any one of clauses 63, or 65-67, wherein the procedure includes diagnostic angiography.

Clause 69: In one example, the method includes clause 68, wherein the procedure includes diagnostic angiography of an ipsilateral external carotid artery.

Clause 70: In one example, the method includes clause 68, wherein the procedure includes diagnostic angiography of an ipsilateral internal carotid artery.

Clause 71: In one example, the method includes any one of clauses 63, or 65-67, wherein the procedure includes treating vasospasm of an ipsilateral internal carotid artery.

Clause 72: In one example, the method include clause 71, wherein treating vasospasm of an ipsilateral internal carotid artery includes pharmacologically treating the vasospasm.

Clause 73: In one example, the method include clause 72, wherein pharmacologically treating the vasospasm includes treating the vasospasm with nimodipine.

Clause 74: In one example, the method includes any one of clauses 63, or 65-67, wherein the procedure includes embolizing a middle meningeal artery.

Clause 75: In one example, the method includes clause 74, wherein the subject suffers from a unilateral chronic subdural hematoma.

Clause 76: In one example, the method includes either one of clauses 74-75, wherein the middle meningeal artery is embolized by a water-insoluble polymer dissolved in dimethylsulfoxide (DMSO).

Clause 77: In one example, the method includes clause 76, wherein the polymer includes ethylene vinyl alcohol (EVOH).

Clause 78: In one example, the method includes any one of clauses 63, or 65-67, wherein the procedure includes infusing a medicant into a middle meningeal artery.

Clause 79: In one example, the method includes clause 78, wherein the subject suffers from chronic migraines.

Clause 80: In one example, the method includes either one of clauses 78-79, wherein the medicant includes lidocaine.

Clause 81: In one example, the method includes any one of clauses 78-80, wherein the medicant is delivered over time.

Clause 82: In one example, the method includes clause 81, wherein the medicant is delivered from a reservoir placed under the scalp or skin.

Clause 83: In one example, the method includes clause 82, wherein the reservoir is placed behind an ear of the subject.

Clause 84: In one example, the method includes clause 83, wherein the reservoir is placed above the mastoid region of the subject.

Clause 85: In one example, the method includes clause 84, wherein the reservoir is placed under the hairline of the subject.

Clause 86: In one example, the method includes any one of clauses 82-85, wherein the reservoir is configured with a tunneled tubing system.

Clause 87: In one example, the method includes any one of clauses 63, or 65-67, wherein the procedure includes embolizing a meningioma.

Clause 88: In one example, the method includes clause 87, wherein the procedure is performed prior to an operation to remove some or all of the meningioma.

Clause 89: In one example, the method includes either one of clauses 87-88, wherein the embolization utilizes embolic coils.

Clause 90: In one example, the method includes any one of clauses 63, or 65-67, wherein the procedure includes embolizing an internal maxillary artery.

Clause 91: In one example, the method includes clause 90, wherein the subject suffers from epistaxis.

Clause 92: In one example, the method includes clause 90, wherein the subject suffers from a tumor.

Clause 93: In one example, the method includes clause 92, wherein the tumor is related to a juvenile nasopharyngeal angiofibroma.

Clause 94: In one example, the method includes clause 92, wherein the tumor is related to a head and neck cancer.

Clause 95: In one example, the method includes any one of clauses 63, or 65-67, wherein the procedure includes electrical stimulation within a middle meningeal artery.

Clause 96: In one example, the method includes clause 95, wherein a powered controller is placed under the scalp or skin of the subject.

Clause 97: In one example, the method includes clause 96, wherein the powered controller is placed behind the ear of the subject.

Clause 98: In one example, the method includes clause 97, wherein the powered controller is placed above the mastoid region Clause 99: In one example, the method includes clause 98, wherein the powered controller is placed under the hairline of the subject.

Clause 100: In one example, the method includes any one of clauses 63, or 65-67, wherein the procedure includes delivery of a medicant from a reservoir, wherein the reservoir is anchored by a stent-like structure implanted within an artery.

While embodiments have been shown and described, various modifications may be made without departing from the scope of the inventive concepts disclosed herein. As previously described, everything described for the right side of the patient can be performed for the left side of the patient. In some cases, the same devices would be utilized.

In other cases, a mirror-image version of the device can be used (for example, the curved sheath 201/securement band 243 assembly).

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

For purposes of the present disclosure and appended claims, the conjunction "or" is to be construed inclusively (e.g., "an apple or an orange" would be interpreted as "an apple, or an orange, or both"; e.g., "an apple, an orange, or an avocado" would be interpreted as "an apple, or an orange, or an avocado, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open-ended terminology, with the same meaning as if the phrase "at least" were appended after each instance thereof.

What is claimed is:

1. A method for accessing one or more arteries in a head and neck area, comprising:
    creating a puncture in an arterial wall of a superficial temporal artery of a subject;
    inserting through the puncture a distal end of a tubular shaft of an access sheath, the shaft further comprising a proximal end comprising a first connection portion, and a sheath lumen extending therethrough and configured for placement of an elongate medical device, the sheath comprising an intermediate portion located between the distal end of the shaft and the proximal end of the shaft, wherein the shaft maintains a curved shape of the sheath lumen at the intermediate portion during placement of the elongate medical device and during a medical procedure;
    adjusting the shaft such that the distal end extends retrogradely within a portion of the superficial temporal artery of the subject;
    hydraulically coupling a distal end of an extension lumen of a resilient access-extension tube to the first connection portion, the extension lumen further comprising a proximal end, the extension lumen extending through the access-extension tube, the access-extension tube further carrying a sealable opening;
    inserting the elongate medical device through the sealable opening and into the extension lumen and advancing the elongate medical device through the extension lumen and the sheath lumen, and advancing the elongate medical device retrogradely through at least some of the superficial temporal artery of the subject; and
    performing the medical procedure utilizing the elongate medical device within the arterial system of the subject.

2. The method of claim 1, wherein the curved shape of the sheath lumen comprises a U-shape.

3. The method of claim 1, wherein the intermediate portion of the sheath is formed by heat setting to maintain the curved shape of the sheath lumen.

4. The method of claim 1, further comprising attaching a holder to the intermediate portion of the shaft to the subject.

5. A method for accessing one or more arteries in a head and neck area, comprising:
    providing a system comprising:
        an access sheath comprising a tubular shaft having a distal end, a proximal end, and a sheath lumen extending therethrough and configured for placement of an elongate medical device, the distal end of the shaft configured for placement through a puncture an arterial wall of a superficial temporal artery of a subject and to extend retrogradely within a section of the superficial temporal artery of the subject, the proximal end of the shaft comprising a first connection portion, wherein an intermediate portion of the sheath is located between the distal end of the shaft and the proximal end of the shaft, wherein the shaft maintains a U-shape of the sheath lumen at the intermediate portion during placement of the elongate medical device and during a medical procedure;
        a resilient access-extension tube having an extension lumen extending therethrough, the extension lumen having a distal end and a proximal end, the distal end of the extension lumen configured to hydraulically couple to the sheath lumen at the first connection portion; and
        a sealable opening carried by the access-extension tube and spaced from the distal end of the extension lumen, the sealable opening configured to allow insertion of the elongate medical device into the extension lumen for advancement through the extension lumen when the access-extension tube is coupled to the access sheath, for passage through the extension tube and the sheath lumen, and into the superficial temporal artery of the subject;
    creating the puncture in the arterial wall of the superficial temporal artery of the subject;
    inserting through the puncture the distal end of the shaft of the access sheath;
    adjusting the shaft such that the distal end extends retrogradely within a portion of the superficial temporal artery of the subject;
    hydraulically coupling the distal end of the extension lumen of the access-extension tube to the first connection portion;
    inserting the elongate medical device through the sealable opening and into the extension lumen and advancing the elongate medical device through the extension lumen and the sheath lumen, and advancing the elongate medical device retrogradely through at least some of the superficial temporal artery of the subject; and
    performing the medical procedure utilizing the elongate medical device within the arterial system of the subject.

6. The method of claim 5, wherein the intermediate portion of the sheath utilizes material memory to maintain the U-shape of the sheath lumen.

7. The method of claim 5, wherein the system further comprises a holder configured to secure a section of the shaft to the subject.

8. The method of claim 5, further comprising:
    accessing an internal maxillary artery branching from the superficial temporal artery of the subject through use of the elongate medical device.

9. The method of claim 8, further comprising:
performing an intervention in a middle meningeal artery branching from the internal maxillary artery of the subject.

10. A method for accessing one or more arteries in a head and neck area, comprising:
creating a puncture in an arterial wall of a superficial temporal artery of a subject;
inserting through the puncture a distal end of a tubular shaft of an access sheath, the shaft further comprising a proximal end, and a sheath lumen extending therethrough and configured for placement of an elongate medical device, the sheath comprising an intermediate portion located between the distal end of the shaft and the proximal end of the shaft, wherein the shaft maintains a curved shape of the sheath lumen at the intermediate portion during placement of the elongate medical device and during a medical procedure; and
inserting the elongate medical device through the sheath lumen, with the sheath lumen at the intermediate portion of the shaft in the curved shape, such that the elongate medical device is delivered retrogradely within a portion of the superficial temporal artery of the subject.

11. The method of claim 10, further comprising:
securing a head band that is coupled to the access sheath around a head area of the subject;
engaging a first portion of the head band above a first ear of the subject adjacent the puncture in the arterial wall of the superficial temporal artery of the subject; and
engaging a second portion of the head band below the first ear of the subject, such that the distal end of the shaft is stabilized.

12. The method of claim 10, wherein the elongate medical device is a guiding catheter.

13. The method of claim 12, further comprising:
advancing a stent through the guiding catheter and into an internal maxillary artery branching from the superficial temporal artery of the subject;
advancing the stent into a middle meningeal artery branching from the internal maxillary artery of the subject; and
causing or allowing the stent to expand within the middle meningeal artery of the subject.

14. The method of claim 12, further comprising:
inserting a microcatheter through the guiding catheter, wherein the microcatheter comprises a microcatheter shaft having a distal end, a microcatheter lumen extending through the microcatheter shaft, and an anchoring stent configured to anchor the distal end of the microcatheter shaft to a blood vessel, and further comprising:
advancing the stent and the distal end of the microcatheter shaft into an internal maxillary artery branching from the superficial temporal artery of the subject;
advancing the stent and the distal end of the microcatheter shaft into a middle meningeal artery branching from the internal maxillary artery of the subject; and
causing or allowing the stent to expand within the middle meningeal artery to anchor the distal end of the microcatheter shaft to the middle meningeal artery of the subject.

15. The method of claim 14, further comprising:
performing infusion of a medicant through the microcatheter lumen and into the middle meningeal artery of the subject.

16. The method of claim 14, further comprising:
implanting a reservoir and a pump coupled to the reservoir within a tunnel beneath the skin of the subject;
hydraulically coupling the pump and the reservoir to the microcatheter lumen; and
performing infusion of a medicant contained within the reservoir through the microcatheter lumen and into the middle meningeal artery of the subject via operation of the pump.

17. The method of claim 16, further comprising:
filling the reservoir with the medicant by puncturing the skin of the subject and passing a needle of a syringe containing the medicant through a port associated with the reservoir, for transfer of the medicant from the syringe to an interior of the reservoir via actuation of the syringe.

18. The method of claim 10, wherein the elongate medical device is a microcatheter.

19. The method of claim 10, further comprising:
performing the medical procedure utilizing the elongate medical device within the arterial system of the subject, wherein performing the medical procedure comprises advancing the elongate medical device through an internal maxillary artery branching from the superficial temporal artery of the subject and into a middle meningeal artery branching from the internal maxillary artery.

20. The method of claim 19, further comprising:
performing fluoroscopy or angiography of at least a portion of the middle meningeal artery with the elongate medical device.

21. The method of claim 19, further comprising:
performing an embolization by expelling an embolic material with the elongate medical device while a distal tip of the elongate medical device is in at least a portion of the middle meningeal artery.

22. The method of claim 21, wherein the embolization comprises embolizing at least a portion of the middle meningeal artery.

23. The method of claim 21, wherein the embolization comprises embolizing at least one artery that branches from the middle meningeal artery.

24. The method of claim 19, further comprising:
performing infusion of a medicant in the middle meningeal artery.

25. The method of claim 10, further comprising:
performing the medical procedure utilizing the elongate medical device within the arterial system of the subject, wherein performing the medical procedure comprises delivering a medicant to an ipsilateral internal carotid artery with the elongate medical device.

26. The method of claim 10, further comprising:
performing the medical procedure utilizing the elongate medical device within the arterial system of the subject, wherein performing the medical procedure comprises embolizing one or more feeder vessels of a tumor with the elongate medical device.

27. The method of claim 10, further comprising:
performing the medical procedure utilizing the elongate medical device within the arterial system of the subject, wherein performing the medical procedure comprises advancing the elongate medical device into an internal maxillary artery branching from the superficial temporal artery of the subject and performing an embolization by expelling an embolic material with the elongate medical device to embolize at least a portion of the internal maxillary artery.

28. The method of claim 10, further comprising:

removing the elongate medical device and the access sheath from the subject;

securing a head band that is coupled to and supporting an expandable member such that the expandable member is placed over the puncture; and expanding the expandable member to provide a force against the puncture.

29. The method of claim 10, wherein the intermediate portion of the sheath is formed by heat setting to maintain the curved shape of the sheath lumen.

30. The method of claim 10, further comprising attaching a holder to the intermediate portion of the shaft to the subject.

\* \* \* \* \*

UNITED STATES PATENT AND TRADEMARK OFFICE
CERTIFICATE OF CORRECTION

PATENT NO. : 12,364,846 B1
APPLICATION NO. : 18/755607
DATED : July 22, 2025
INVENTOR(S) : Adam S. Arthur et al.

Page 1 of 1

It is certified that error appears in the above-identified patent and that said Letters Patent is hereby corrected as shown below:

In the Claims

Column 28, Claim 5, Line 9: insert -- in -- before "an arterial wall"

Column 31, Claim 30, Line 12: insert -- to secure the shaft -- after "immediate portion of the shaft"

Signed and Sealed this
Eighteenth Day of November, 2025

John A. Squires
*Director of the United States Patent and Trademark Office*